(12) United States Patent
Lu

(10) Patent No.: US 8,691,094 B2
(45) Date of Patent: Apr. 8, 2014

(54) METHOD AND SYSTEM FOR TREATING DOMESTIC SEWAGE AND ORGANIC GARBAGE

(75) Inventor: Ming Lu, Hong Kong (HK)

(73) Assignee: Huge Asia Limited, Hong Kong (HK)

( * ) Notice: Subject to any disclaimer, the term of this patent is extended or adjusted under 35 U.S.C. 154(b) by 373 days.

(21) Appl. No.: 13/141,082

(22) PCT Filed: Nov. 4, 2010

(86) PCT No.: PCT/CN2010/078402
§ 371 (c)(1),
(2), (4) Date: Jun. 21, 2011

(87) PCT Pub. No.: WO2011/054298
PCT Pub. Date: May 12, 2011

(65) Prior Publication Data
US 2011/0315626 A1    Dec. 29, 2011

(30) Foreign Application Priority Data

Nov. 4, 2009    (CN) .......................... 2009 1 0209371

(51) Int. Cl.
*C02F 3/28*    (2006.01)
*C02F 11/04*   (2006.01)
*C02F 9/14*    (2006.01)

(52) U.S. Cl.
USPC .......... 210/603; 210/612; 210/173; 210/175; 210/259; 210/903; 210/906

(58) Field of Classification Search
USPC ......... 210/603, 612, 621, 622, 623, 173, 175, 210/252, 259, 903, 906
See application file for complete search history.

(56) References Cited

U.S. PATENT DOCUMENTS 4,053,399 A * 10/1977 Donnelly et al. ............. 210/706
4,326,874 A *  4/1982 Burklin ............................ 71/9
6,942,798 B2* 9/2005 Miller, III .................... 210/603

FOREIGN PATENT DOCUMENTS

| CN | 2358998 | 1/2000 |
|---|---|---|
| EP | 0114296 | 8/1984 |
| JP | 10216785 | 8/1998 |
| JP | 2005-261390 A * | 9/2005 |

OTHER PUBLICATIONS

International Search Report of PCT/CN2010/078402, mailed Feb. 10, 2011.

* cited by examiner

*Primary Examiner* — Fred Prince

(57) ABSTRACT

A method and system for treating domestic sewage and organic garbage are provided. The method comprises the steps of: multi-phase separation, retting, generating sewage gas, and optional biological denitrification and dephosphorization, which can convert the domestic sewage and organic garbage into clear water, sewage gas, organic manure and sludge. The system comprises a multi-phase separation device, a retting device, a sewage gas generating device and a biological denitrification and dephosphorization device, which can treat the domestic sewage and organic garbage effectively and environmental friendly to achieve a reduction in pollution emission.

27 Claims, 19 Drawing Sheets

METHOD AND SYSTEM FOR TREATING DOMESTIC SEWAGE AND ORGANIC GARBAGE

FIELD OF THE PATENT APPLICATION

The present patent application relates to a method and a system for treating domestic sewage and organic garbage, which can be used to treat the domestic sewage and organic garbage effectively and environmentally friendly to achieve a reduction in pollution emission.

BACKGROUND

With the rapid development of cities, more and more garbage and domestic sewage are generated. The garbage or domestic sewage includes harmful ingredients which will be danger to the atmosphere, water and earth, affecting ecological environment of cities and harming peoples health. Most cities in China have also been surrounded by garbage and domestic sewage. Therefore, garbage and domestic sewage treatment have become a major project in environmental protection. Currently, the garbage and domestic sewage are often treated separately.

Landfilling and incineration are two main garbage disposal methods. However, landfilling will occupy a large area, the site for landfilling is difficult to choose, and it is also difficult to recycle useful resources in the garbage in landfilling. Moreover, leachate and gas generated during the landfilling process are harmful to the surrounding environment. At the same time, the initial investment and operating costs of the landfilling become higher and higher with the advancing environmental standard. Wastes incineration can maximize waste reduction and decontamination. However, due to the expensiveness of its initial investment and operating costs, the secondary pollution of the burning exhaust, and the high requirement for the heat value and the moisture content of the raw materials, the method of the waste incineration may not be appropriate for treating organic garbage.

Fecal sewage treatment mainly uses the natural emission method that discharges the fecal sewage into rivers directly, or discharges the fecal sewage into water pipes after separating the precipitate by using the septic tank. Alternatively, an aerobic biological aeration process or an A2/O sewage treatment process can be used. However, area required for a sewage treatment plant is large; and it is difficult to solve the problem of air pollution and sludge emission. In addition, the waste recycling is improper, and actually has caused the waste of resources.

People have done a lot of research for solving above-mentioned problems such as environment pollution, inappropriate waste disposal, resource waste and etc.

Chinese patent publication number CN1314313A discloses a device for comprehensive treatment of fecal sewage and organic garbage. It separates feces and sewage from fecal sewage by a flotation process and by an overflow method in feces and water separating tanks correspondingly. The separated feces overflow into storage tanks. The organic waste is ducted into the storage tanks after crushed by s crusher. Then the feces and organic waste are fermented in the fermentation tanks to produce biogas. In this method, the separated and crushed feces need an anaerobic digestion process directly with a long reaction time and a low efficiency. Particularly, some substances that are difficult to digest in the anaerobic environment need a relatively longer digestive time. In addition, there are still some pollutants that are inappropriate to discharge directly after producing biogas.

Chinese patent publication number CN 101191116A discloses a combined-type fermentation pool, which is composed of retting pool equipped with heat exchangers and inside recirculation type biogas reactor. Straw, grass, processed fruit dregs and medicine dregs, and other solid form or sticky raw materials are retted directly in the retting pool. The acidification liquid from the fermentation, which is ducted into the biogas reactor through the grid of the bottom of the retting pool, is reacted to produce biogas by anaerobic fermentation. This combined-type fermentation pool with large area, long reaction time and external system contact is not suitable for the treatment of the daily sewage. The retting pool and the biogas reactor are always communicated with each other, which is not good for the occurrence of anaerobic digestion reaction, difficult to control, and produces gas with low efficiency in the biogas reactor. Additionally, as mentioned above, there are still some pollutants that are inappropriate to discharge directly after producing biogas.

Therefore, a more effective method and system are desired, which can treat domestic sewage and organic garbage efficiently and environmentally friendly, so as to achieve the goal of low pollution, or even nearly no pollution in waste discharging.

SUMMARY

The present patent application provides a method and a system for treating domestic sewage and organic garbage, which can treat the domestic sewage and organic garbage effectively and environmental friendly to achieve the goal of low pollution, or even nearly no pollution in waste discharging.

In one aspect, the present patent application provides a method for treating domestic sewage and organic garbage. The method includes:

(a) multi-phase separation: separating the domestic sewage into upper clear liquid, upper floating liquid, sediment liquid, grating separated substances, and exhaust gas through a multi-phase separation process, mixing and crushing the upper floating liquid, the grating separated substances and the organic garbage to form a mixture, and mixing the sediment liquid with the mixture to form high-concentration sewage;

(b) retting: retting the multi-phase separated high-concentration sewage to form retted material;

(c) generating sewage gas: using the upper floating liquid of the domestic sewage and the retted material to generate sewage gas and then discharging the sewage gas; and (d) optional biological denitrification and dephosphorization: treating at least one of the water generated in step (c) and the upper clear liquid obtained in step (a) with a biological denitrification and dephosphorization process, and discharging clean water and organic fertilizer.

In some embodiments of the present patent application, the retting is performed by at least three retting digestion units connected in parallel with each other.

In an embodiment of the present patent application, scum and/or sludge that is difficult to be digested in the process of generating sewage gas or biological denitrification and dephosphorization is returned to the step of retting to retting again.

In another aspect, the present patent application further provides a system for treating domestic sewage and organic garbage. The system includes a multi-phase separation device, a retting device, a sewage gas generating device and an optional biological denitrification and dephosphorization device. The multi-phase separation device, the retting device, the sewage gas generating device and the optional biological denitrification and dephosphorization device is connected to one another in series.

In another aspect, the present patent application further provides a multi-phase separation device for separating domestic sewage. The multi-phase separation device includes a domestic sewage entrance, a gravel separation chamber, a gravel exit, an auto-separating grating machine made of an irregular-shaped grating and a separation rake, a grating separated substance exit, an upper floating chamber, an upper clear liquid chamber, and an optional upper clear liquid regulation tank connected to the upper clear liquid chamber.

In another aspect, the present patent application further provides a multi-phase separation method for separating domestic sewage. The method includes:

(a) separating gravel from the domestic sewage by a sloping method;

(b) obtaining grating separated substances by separating with an irregular-shaped grating;

(c) adsorbing floating substances in the vertical down-flowing sewage by micro-bubbles produced by a micro-bubble producer to form upper floating liquid, and then draining off the upper floating liquid; and/or using the sludge to regulate and absorb the organic pollutants to form upper floating liquid with a lighter specific gravity, and then draining off the upper floating liquid;

(d) changing orientation of the down-flowing sewage at the bottom of a clapboard located between an upper floating chamber and an upper clear liquid chamber, so that the sewage flows into the upper clear liquid chamber while the sediment stays at a bottom, and then draining off the sediment liquid; and (e) draining off the upper clear liquid formed by the up-flowing sewage.

The method and system for treating domestic sewage and organic garbage of the present patent application can be used widely. The method of the present patent application is an all-biotechnology process and is performed in an enclosed environment using complete sets of equipments of factory production, without leakage and secondary pollution.

BRIEF DESCRIPTIONS OF THE DRAWINGS

DETAILED DESCRIPTION

The domestic sewage herein refers to any sewage in the process of human life. It is one of the main pollution sources for water. Domestic sewage, for example, is fecal sewage and/or washing sewage. Domestic sewage contains a lot of organic compounds, such as cellulose and starch, carbohydrate, fat and protein, etc. Also it often contains pathogenic bacteria, viruses and parasitic ovum; inorganic salt, such as chloride, sulfate, phosphates, bicarbonate and sodium, potassium, calcium, magnesium, and etc. The general characteristics are that it contains high concentration of nitrogen, sulfur and phosphorus and is likely to generate stinking substances under the action of the aerobic bacteria.

Organic garbage herein generally refers to domestic garbage mainly composed of organics, mainly including paper, fiber, woods and kitchen waste. The kitchen waste is composed of the leftovers of families, hotels and cafeterias, which is composed of degradable organics that has high moisture content and is easy to corrupt. More than 50% of urban domestic garbage is organic waste, and increasing year by year.

Figure 1:
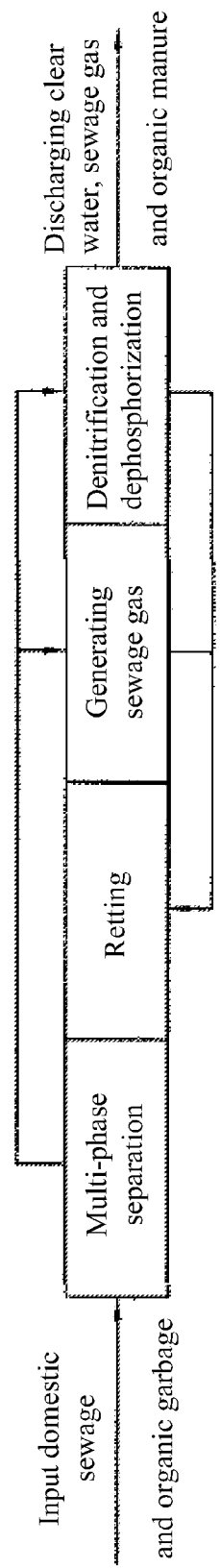
FIG. 1 is a flowchart of a method for treating domestic sewage and organic garbage.

Referring to FIG. 1, a method for treating domestic sewage and organic garbage according to the present patent application includes the steps of multi-phase separation, retting, generating sewage gas, and optional biological denitrification and dephosphorization. The method in this embodiment is an all-biotechnology process and is performed in an enclosed environment using complete sets of equipments of factory production, without leakage and secondary pollution.

1. Multi-Phase Separation Device

Figure 2:
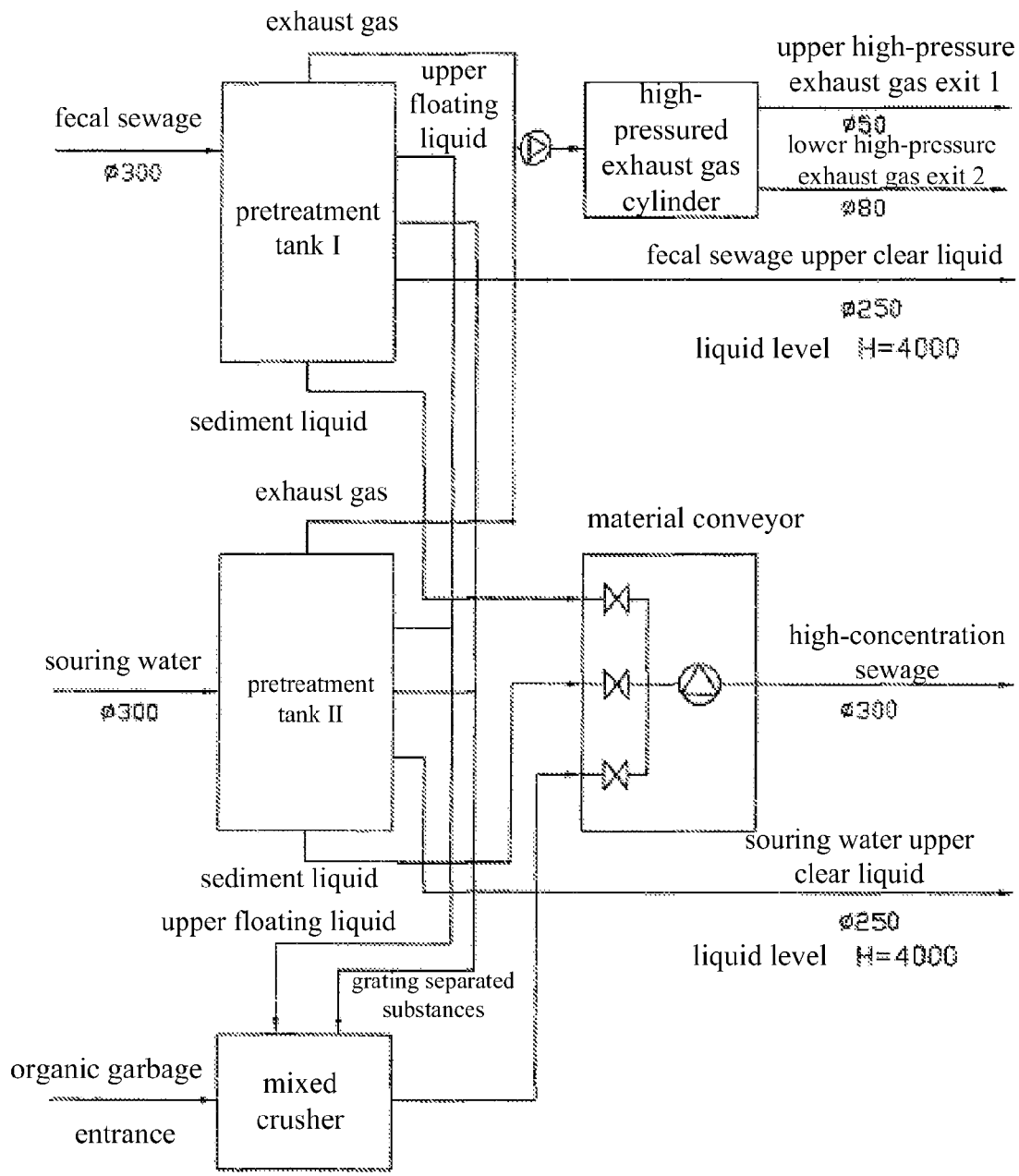
FIG. 2 is a flowchart of the process of multi-phase separation preformed by a multi-phase separation device.

Referring to FIG. 2, a multi-phase separation device according to the present patent application is provided, the device including a pretreatment tank I, a pretreatment tank II, a mixture crusher, a high-pressure waste gas container and a material conveyor. There is no connection between the pretreatment tank I and the pretreatment tank II, and there is no connection between the high-pressured waste gas container and the material conveyor. The pretreatment tank I and the pretreatment tank II are both connected to the mixture crusher, the high-pressure waste gas container and the material conveyor. The pretreatment tank I and the pretreatment tank II are separation devices. The pretreatment tank I is used to separate the fecal sewage, and the pretreatment tank II is used to separate the scouring water. The pretreatment tank I defines a fecal sewage entrance, a fecal sewage exhaust gas exit, a fecal sewage upper clear liquid exit, a fecal sewage upper floating liquid exit, a fecal sewage grating separated substance exit and a fecal sewage sediment liquid exit. The pretreatment tank II defines a scouring water entrance, a scouring water exhaust gas exit, a scouring water upper clear liquid exit, a scouring water upper floating liquid exit, a scouring water grating separated substance exit and a scouring water sediment liquid exit. The mixture crusher defines an organic garbage entrance, a fecal sewage/scouring water upper floating liquid entrance, a fecal sewage/scouring water grating separated entrance and a mixing crushed material exit. The high-pressure waste gas container defines a fecal sewage/scouring water exhaust gas entrance, a first upper high-pressure exhaust gas exit 1, and a second upper high-pressure exhaust gas exit 2. The material conveyor includes a mixer and defines a fecal sewage/scouring water sediment liquid entrance, a mixing crushed material entrance and a high-concentration sewage exit.

Figure 3:
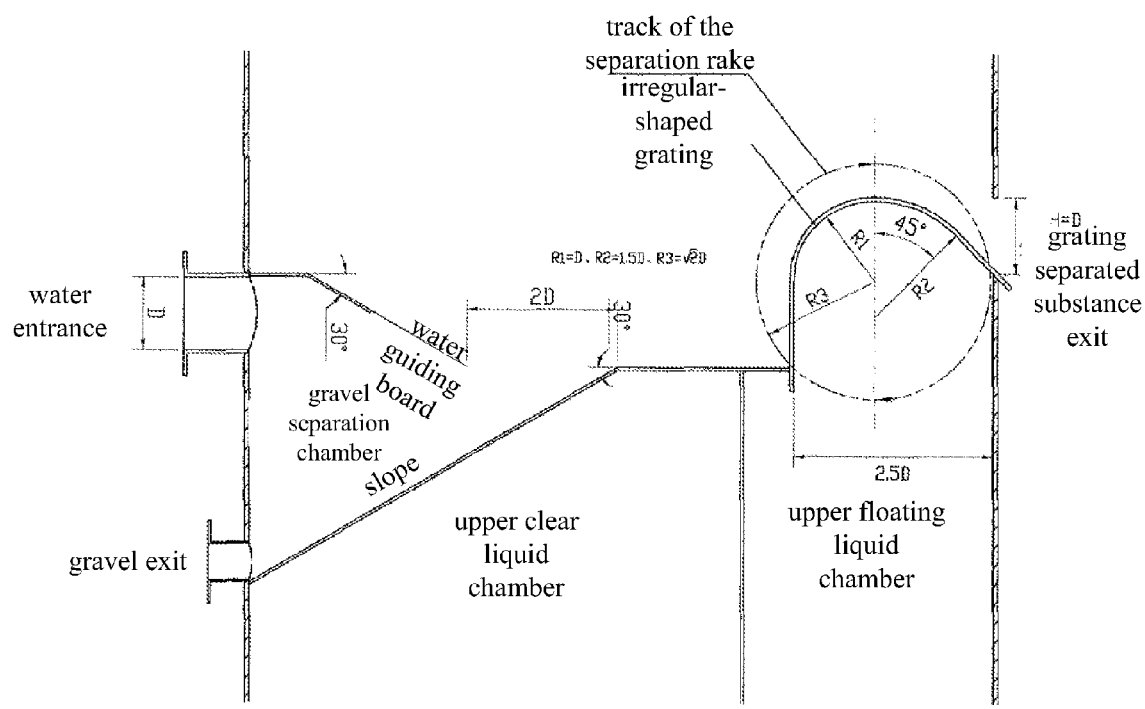
FIG. 3 is a schematic diagram of an auto-separating grating machine and gravel separation.

The pretreatment tank has a gravel separation device and an auto-separating grating machine therein, and includes a domestic sewage entrance, a gravel separation chamber, a gravel exit, an irregular-shaped grating, a grating separated substance exit, an upper floating chamber and an upper clear liquid chamber, as shown in FIG. 3. The domestic sewage entrance is located at the top of the gravel separation chamber, and the gravel exit is located the bottom of the gravel separation chamber. The gravel separation chamber includes a slope for separating the gravel. The angle formed between the slope and a horizontal plane is not less than 30 degrees. In a preferred embodiment, the angle is 30 degrees. The auto-separating grating machine includes an irregular-shaped grating. In consideration of the irregular-shaped grating having a complicated production process and high costs, the auto-separating grating machine can be molded with engineering plastic to reduce cost. The upper floating chamber and upper clear liquid chamber are located at the bottom of the pretreatment tank, and are separated by a vertical clapboard. The volume of the upper clear liquid chamber is not less than that of the upper floating chamber. In this embodiment, the ratio of the volume of the upper clear liquid chamber to the volume of the upper floating chamber is 3. The middle portion of the upper floating chamber includes a micro-bubble producer. In another embodiment, a sludge regulation releaser can be a substitute or a supplement of the micro-bubble producer for releasing anaerobic bottom sediment and bottom liquid produced in the sewage gas generating process, for example, input by a pump (such as a Nikuni pump), to achieve anaerobic sludge regulation, and the micro-bubble producer itself can be used as the sludge regulation releaser.

The gravel separation device can be used with a gravel extracting machine. The gravel extracting machine can be designed according to the principle of gas extraction and is easy to operate.

In another embodiment, an assisting tank is added to locate before the pretreatment tank. The assisting tank includes a gravel separation device and an auto-separating grating machine, while the pretreatment tank omits the gravel separation device and auto-separating grating machine. Such design can reduce the water level loss after the liquid-phase separation.

The mixture crusher includes three rolls and two parallel high speed rotary tips. The first roll is horizontal, and the second and third rolls are vertical. The mixture crusher further includes a high speed rotary crusher.

In another embodiment, the multi-phase separation pretreatment device further includes at least one upper clear liquid regulation tank, connected to the upper clear liquid chamber. The volume of each upper clear liquid regulation tank is 25 cubic meters. The peak storage of the upper clear liquid regulation tank is 3 times larger than the average amount of the water, and supplies the stored water to the outside at a valley value. The regulation time of the upper clear liquid regulation tank can last 4 hours, for example, meeting the system requirement.

In another embodiment, a blower, such as Roots blower, is located between the pretreatment tank and the high-pressure waste gas container, as shown in FIG. 2. The blower can prevent peculiar smell from escaping from the system effectively.

Method

During the multi-phase separation process, the pretreatment tank I and the pretreatment tank II both use the auto-separating grating machine to achieve preliminary solid-liquid-gas phase separation of the domestic sewage. More specifically, the pretreatment tank I separates the fecal sewage into fecal sewage exhaust gas, upper clear liquid, upper floating liquid, sediment liquid and grating separated substance. The pretreatment tank II separates the scouring water into scouring water exhaust gas, upper clear liquid, upper floating liquid, sediment liquid and grating separated substance. The multi-phase separation process includes the steps as follows, as shown in FIG. 3:

When the domestic sewage is conveyed into the system, utilizing the principle that the gravel has the greatest specific gravity, the slope can separate the gravel from the domestic sewage. The gravel with a diameter larger than 2 millimeters can be separated by the slope and taken out from the system by a screw lifting device.

The gravel-removed domestic sewage will be separated by the auto-separating grating machine. The auto-separating grating machine includes an irregular-shaped grating and a separation rake. The irregular-shaped grating includes a vertical section, an arc section and a slant section. The separation rake is driven by a machine and moves circumferentially. The separation rake takes the separated substance from the vertical section to the arc section continuously, and then takes the separated substance to the grating separated substance exit via the slant section. The separated substance then will be conveyed into the crusher. The auto-separating grating machine can keep working continuously, and the pitch between each two neighboring gratings is less than 4 millimeters. The domestic sewage in above processes can flow transversely above the pretreatment tank.

Passing through the grating machine, the domestic sewage will flow down to the upper floating chamber (gas floating chamber). The upper floating chamber includes a micro-bubble producer. The micro-bubble producer treats the compressed exhaust gas as gas source and jets the compressed exhaust gas aslant into a circular cavity including a porous wall. The gas and liquid in the cavity are mixed and rotated with a high speed. The porous wall changes the sheared and centrifuged water and gas into micro-bubbles. The micro-bubbles can be used to absorb the floating material in the domestic sewage and float them to a sloped sediment collection portion. The upper floating liquid including absorbed floating material can be discharged from the system. The micro-bubble producer is located in the middle portion of the upper floating chamber, and the processed domestic sewage will keep flowing downward after being treated by the micro-bubble producer.

When the domestic sewage flows down to the bottom of the pretreatment tank, the clapboard located between the upper floating chamber and the upper clear chamber can reduce the flowing velocity of the domestic sewage and change the orientation of the domestic sewage to make the domestic sewage flow up into the upper clear chamber. As such, the sediment will stay at the bottom of the pretreatment tank, and the sediment liquid can be discharged from the pretreatment tank via the sediment liquid exit of the pretreatment tank.

When the domestic sewage flows up into the upper clear chamber, the domestic sewage can be discharged from the pretreatment tank as upper clear liquid. To separate the upper clear liquid more effectively, the up-flowing distance or the down-flowing distance of the domestic sewage can be more than 5 meters. The values of the COD (chemical oxygen demand, in units of mg/L) of the upper clear liquid, T/P (total phosphorus pollutants, in units of mg/L) of the upper clear liquid and SS (suspended substance, in units of mg/L) of the upper clear liquid are reduced significantly.

The upper floating liquid and the upper clear liquid are separated by the clapboard, so that the discharged exits can have the same height. The multi-phase separation pretreatment device can efficiently utilize the principle of the up and down movement of the water, and therefore, the requirement on the static time is extremely low. In addition, except that the sediment liquid is discharged form the bottom of the pretreatment tank, most of domestic sewage exits are only about 200 millimeters lower than the domestic sewage entrances, and therefore, the reduction of the water level is extremely small, and that would reduce the cost of raising water level in the post-treatment process.

Because the needed amount of the upper floating liquid in the following mixing process is larger than the outputting amount of the upper floating liquid, the domestic sewage in the bottom can be separated into sediment liquid easily and float upward hardly, and the sediment also can be discharged continuously. As such, the quality of upper clear liquid can be ensured, and no additive is required in the whole liquid separation process.

If the amount of the mixture of the upper floating liquid and the sediment liquid is set as a, and the amount of the upper clear liquid is set as b, then the total amount of water is a+b. In a preferred embodiment, the ratio between the amount of the mixture of the upper floating liquid and the sediment liquid a and the total amount of water (a+b) is not more than 5%.

The organic garbage enters the mixture crusher via the material entrance. The grating separated substance of the fecal sewage separated by the pretreatment tank I and the grating separated substance of the scouring water separated by the pretreatment tank II enter the mixture crusher. The three rolls and two parallel high speed rotary tips crush the organic garbage and the grating separated substance. The first roll crushes some small gravel and flattens the crushed gravel. The second roll rolls the crushed gravel into small solid bar. The third roll rolls the small solid bar into a particulate solid substance. The solid substance is combined with the upper floating liquid auto-flowing from the water entrance of the mixture crusher. The combined material then enters the cavity of the high speed rotary crusher and is crushed and converted into a liquid state. The crushed and combined liquid is discharged from the mixture crusher after filtered by a filter with 50 meshes. The crushed and combined liquid and two tanks of sediment liquid are combined entering the conveyor. The proportion of crushed combined material liquid and the sediment liquid is controlled by a valve of the conveyor. Concentration of the solid material (i.e. organic contaminant) is weighed no more than 40%, so that the screw pump can discharge high-concentration sewage conveniently.

The exhaust gas produced in the pretreatment tank I and the pretreatment tank II are discharged from the exhaust gas exit and are used as the gas source of the gas pump. The check valve of the gas pump compresses the exhaust gas and conveys the compressed exhaust gas to the high-pressure waste gas container with a height of more than 4 meters. The high-pressure waste gas container is located perpendicularly, and therefore, the gas including domestic sewage and particulate substance will stay at the bottom of the cylinder. The cylinder defines an upper gas exit and a lower gas exit. The gas discharged from the upper gas exit is used in an aerobic agitation process performed in the biological denitrification and dephosphorization device, and the gas discharged from the lower gas exit is used in an aerobic agitation process during the initial stage of the retting reaction, or the gas source of the micro-bubble producer is conveyed back into the upper floating chamber directly.

The exhaust gas exits of the pretreatment tank I and the pretreatment tank II are communicating with the inner cavity of the mixture crusher via the grating separation channel. The material entrance of the mixture crusher is in a negative pressure state, and therefore, there will not be any leakage problems of peculiar smells at the material entrance.

The gas pump is driven by a frequency conversion motor and controlled by a pressure sensor so that the gas pump is always in a continuously running state. Therefore, there will be gas source being discharged from the exhaust gas exit for the pretreatment continuously, and the material entrance will always be in a negative pressure state. The controlling method for the frequency conversion motor is as follows: when the pressure of a pressure sensor reaches a threshold, a pressure signal is output to adjust the power output frequency of the frequency converter. When the pressure of the pressure sensor becomes lower, the speed of the frequency conversion motor will slow down correspondingly. The gas pump is in a continuously running state.

Except for the manual operation of feeding the organic garbage, the rest of the operations of the multi-phase separation device are automatic processes.

In a further embodiment, the anaerobic bottom sediment and the anaerobic bottom liquid produced in the sewage gas generating process can be used in the multi-phase separation device to regulate the anaerobic bottom sediment and improve the separation effect of pretreatment.

Figure 4:
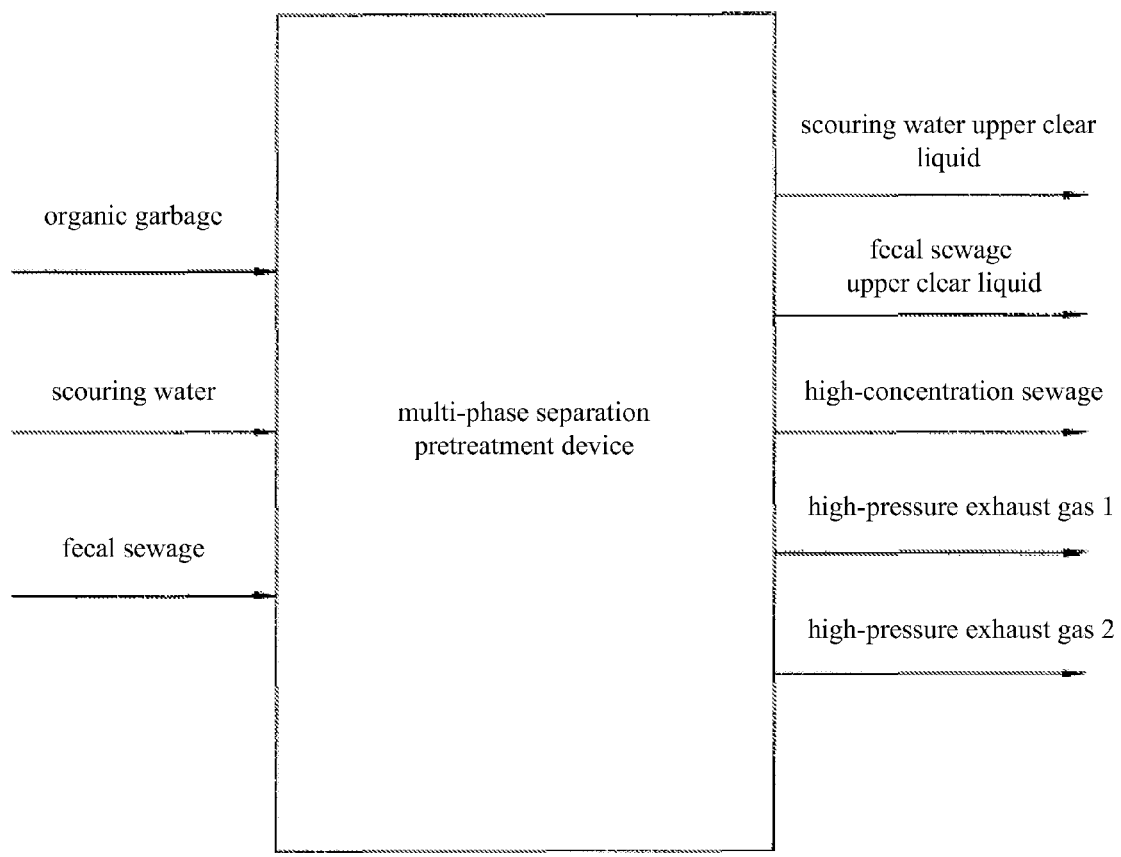
FIG. 4 is a block diagram of the multi-phase separation device.

Referring to FIG. 4, in this embodiment, the organic garbage, the fecal sewage and the scouring water are separated into scouring water upper clear liquid, fecal sewage upper clear liquid, high-concentration sewage, high-pressure exhaust gas 1 and high-pressure exhaust gas 2 by the multi-phase separation device.

The experiments using different media in the micro-bubble producer are as follows: the micro-bubble producer is located in the middle portion of the upper floating chamber and is added the compressed air directly to produce micro-bubble, so as to enhance the separation capacity of the upper floating chamber. The measured COD value of the upper clear liquid is about 400 mg/L. The measured SS value of the upper clear liquid is about 300 mg/L. These values indicate that the gas floating capacity is limited without flocculants. In another embodiment, a Nikuni pump is added and communicated with the entrance of the micro-bubble producer, and the bottom sediment and the bottom liquid in the secondary deposition device, or the bottom sediment and the bottom liquid in the sewage gas generating device are added into the micro-bubble producer. The flow rate of the Nikuni pump is 0.5 to 2 $m^3$/h, and the lift of the Nikuni pump is 15 meters. In the two experiments, the COD value and SS value are measured after 4 hours. When the bottom sediment and the bottom liquid in the secondary deposition device have been added into the micro-bubble producer, the COD value reduces to 320 mg/L, and the SS value reduces to 240 mg/L. In addition, the pollution parameters of the nitrogen and phosphorus are also reduced because of the nitrifying bacteria and polyphosphate bacteria in the aerobic sludge. However, a small amount of sediment is found in the upper clear liquid, which limits the reduction of the SS value. When the bottom sediment and the bottom liquid in the sewage gas generating device have been added into the micro-bubble producer, the COD value becomes less than 200 mg/L, and the SS value becomes less than 160 mg/L. However, the separation of the nitrogen pollutants is not significant. The COD value of the sediment liquid is significantly higher than that of the floating liquid because of the colloid shell of the anaerobic sludge having a better absorption capacity than that of the aerobic sludge. Furthermore, the settlement of the anaerobic sludge is better than that of the aerobic sludge. However, the anaerobic sludge has little effect on separating and absorbing the dispersed oil droplets in the domestic sewage. In this experiment, the anaerobic sludge is preferred because that the anaerobic sludge has the most significant effect on separation in the pretreatment.

2. Retting
Device

Figure 5:
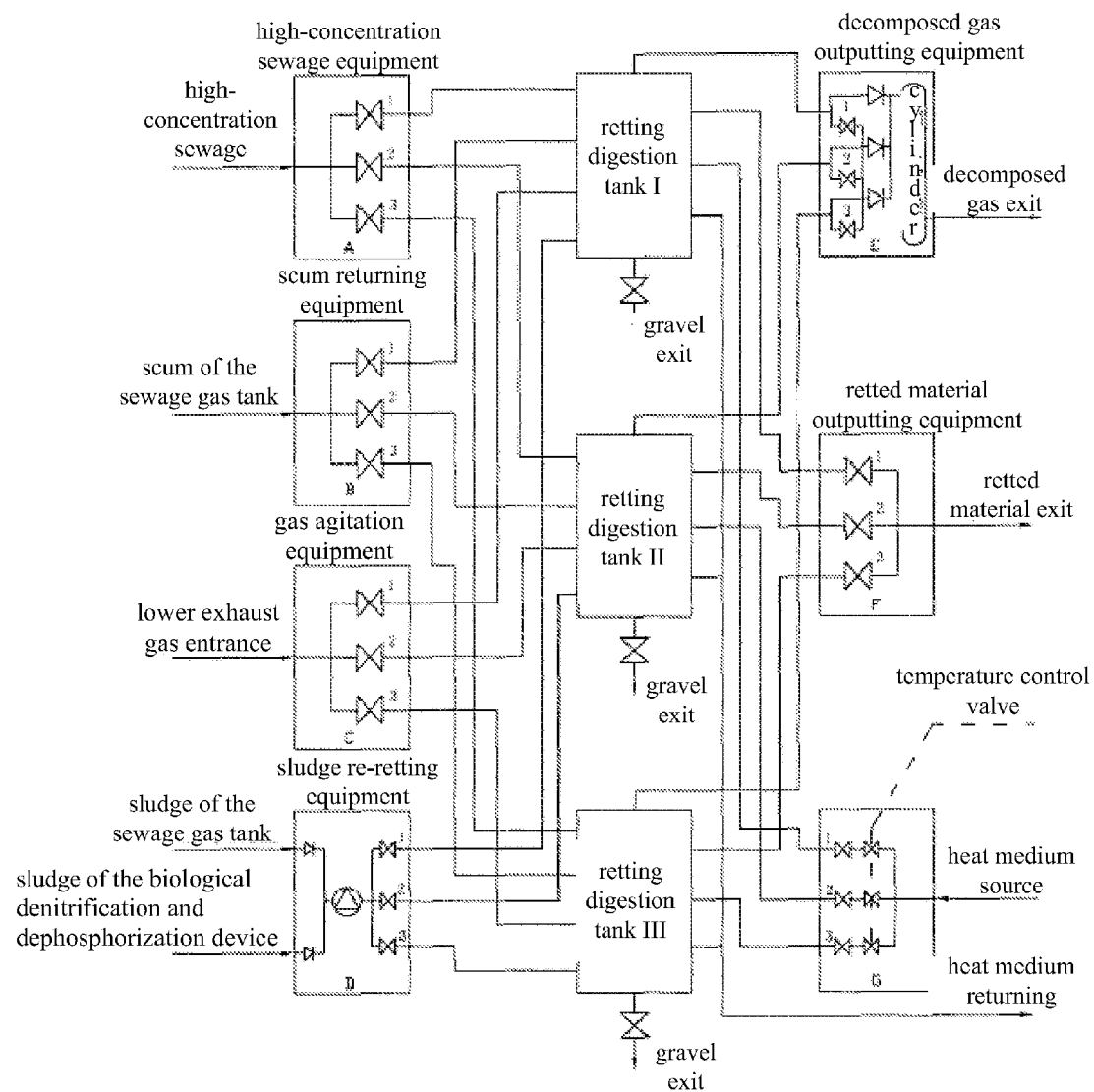
FIG. 5 is a flowchart of the process of retting preformed by a retting device.

Referring to FIG. 5, in an exemplary embodiment, a retting device includes a retting digestion tank and seven sets of equipments. The seven sets of equipments include a high-concentration sewage equipment A, a scum returning equipment B, a gas agitation equipment C, a sludge re-retting equipment D, a decomposed gas outputting equipment E including a gas tank, a retted material outputting equipment F and a temperature control equipment G. The seven sets of equipments include seven valves A, B, C, D, E, F, and G respectively. The seven sets of equipments are connected to the retting digestion tank, and the seven sets of equipments are not connected to each other. The high-concentration sewage equipment A, the scum returning equipment B, the gas agitation equipment C, the sludge re-retting equipment D, and the temperature control equipment G are inputting equipments, which input the high-concentration sewage, the scum of the sewage gas tank, the high-pressure exhaust gas 2, the sludge of the sewage gas tank/denitrification and dephosphorization tank, and the heat medium source into the retting digestion tank. The remained equipments are outputting equipments and output the decomposed gas and the retted material produced in the retting digestion tank to the following process. In addition, the retting digestion tank further defines a heat medium returning entrance, conveying the heat generated in the retting reaction to the following process. The retting digestion tank further defines a gravel exit to discharge the gravel residue with little organics.

The parallel connection of the retting digestion tanks is determined by the number of the retting digestion tanks. In this embodiment, there are at least three retting digestion tanks connected in parallel with each other. The number of the valves in each equipment corresponds to the number of the parallel retting digestion tanks. Therefore, there are at least three valves in each equipment of the seven sets of equipments. The number of the parallel retting digestion tanks is decided by the volume and the concentration of the domestic sewage. To keep the system running continuously, the retting reaction time should last 2 to 3 days, with one retting digestion tank outputting material and one retting digestion tank inputting material. If the number of the retting digestion tanks increases, the parallel valves in each corresponding input/output equipment should be added accordingly.

In this embodiment, there are three retting digestion tanks I, II, III connected in parallel with each other, and each equipment includes three valves to cooperate with the three retting digestion tanks respectively. That is, the high-concentration sewage equipment A includes three valves A1, A2, A3, the scum returning equipment B includes three valves B1, B2, B3, the gas agitation equipment C includes three valves C1, C2, C3, the sludge re-retting equipment D includes three valves D1, D2, D3, the decomposed gas outputting equipment E includes three valves E1, E2, E3, the retted material outputting equipment F includes three valves F1, F2, F3, and the temperature control equipment G includes three valves G1. G2, G3.

Figure 6:
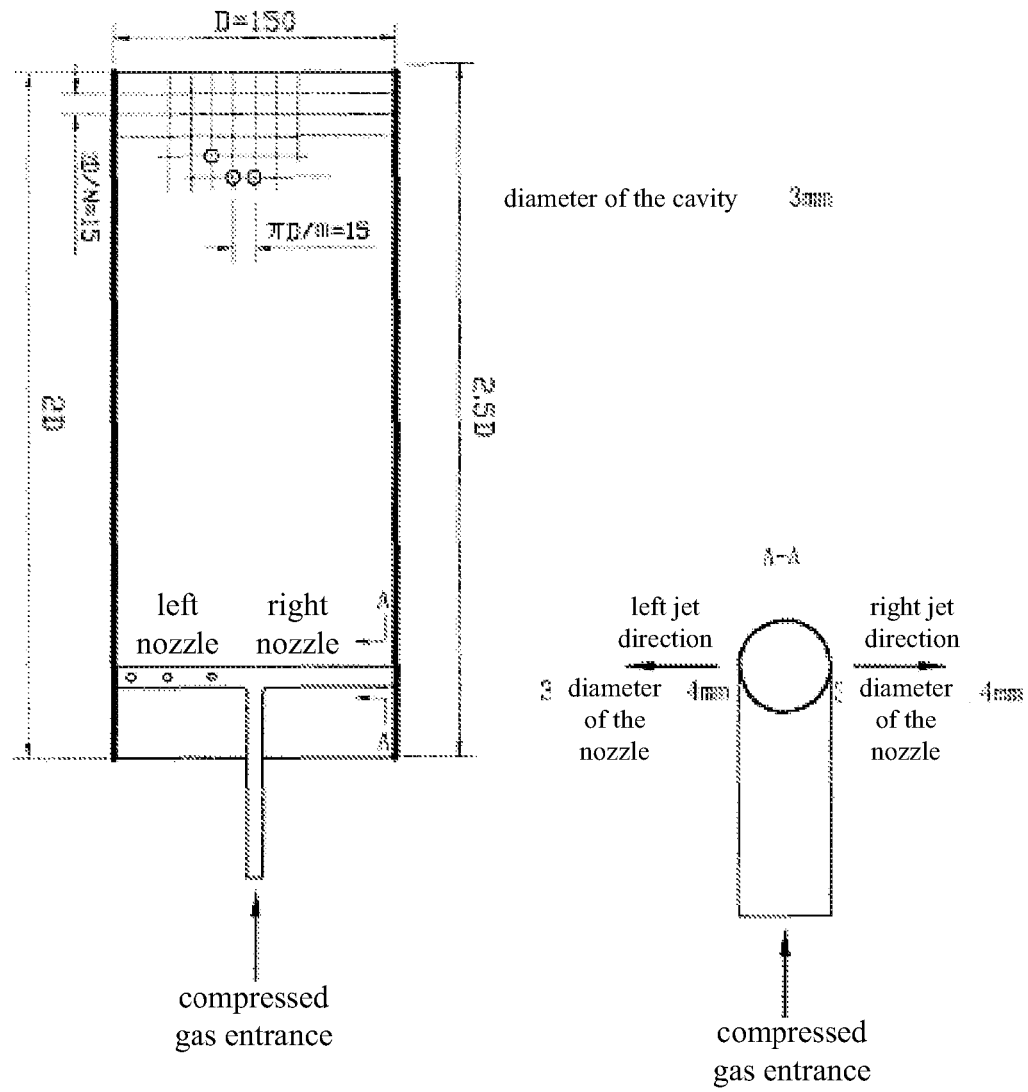
FIG. 6 is a block diagram of a powerful gas agitator.

Each retting digestion tank includes a powerful gas agitator located in the middle bottom of the retting digestion tank, to increase oxygen during an agitation process in an initial stage of the retting reaction, as shown in FIG. 6. The powerful gas agitator is designed according to the principle that the gas jetted from the porous wall to form centrifugal micro-bubble. The diameter of the nozzle of the powerful gas agitator is determined according to that of the cavity of the retting digestion tank. The bottom of the cavity of the retting digestion tank includes an inclined fan-shaped plate. When the gas is jetted, not only the micro-bubble can be formed centrifugally form the porous wall, but also the sludge in the retting digestion tank can be rolled up and be discharged from the upper exit of the cavity. The rolled area of the powerful gas agitator can reach 6 m².

Method

During the parallel retting reaction process, the high-concentration sewage separated in the multi-phase separation process is conveyed into the retting digestion tank via the high-concentration sewage equipment A. One valve C of the gas agitation equipment C is opened, and the exhaust gas produced in the multi-phase separation process is conveyed into the gas agitation equipment C. Therefore, the powerful gas agitator can achieve an aeration agitation process. In the initial stage of the retting reaction, the adsorption and hydrolysis oxidation time is only one hour. The retting reaction is an aerobic retting digestion reaction:

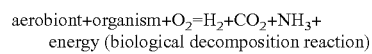
energy (biological decomposition reaction)

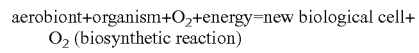
$O_2$ (biosynthetic reaction)

The valve C is closed, and then the oxygen in the system will be consumed gradually. The above biological reactions will stop when the oxygen in the system have been consumed completely, and over 70 percent of the organics are absorbed, hydrolyzed and oxidized by the aerobiont. When the living things are at an anoxic state, the facultative anaerobe depending on internal respiration will replace aerobiont and decompose the organics to form $CO_2$, $H_2O$, $NH_3$ and polysaccharides. When the biological environment is conducive to anaerobe, the following principal biological reactions will take place resulting the following products:

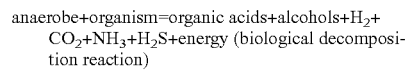
$CO_2+NH_3+H_2S$+energy (biological decomposition reaction)

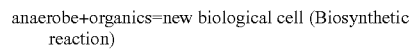
reaction)

Figure 7:
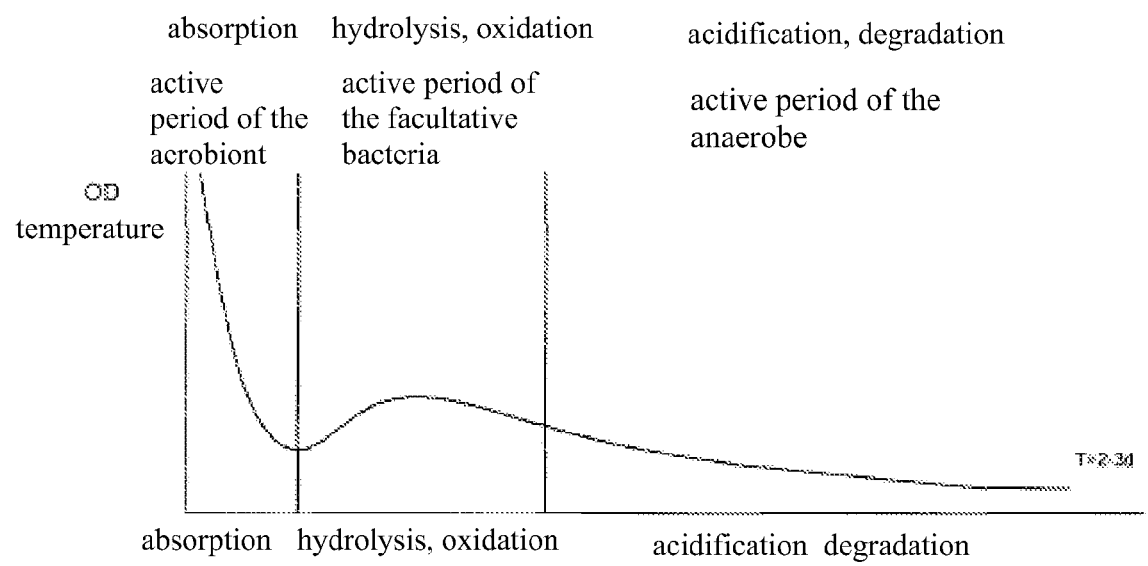
FIG. 7 is a coordinate diagram illustrating the biological activity during the retting process.

Therefore, the reaction taking place in the retting digestion tank actually includes absorption reaction reacted in the active period of the aerobiont, hydrolysis/oxidation reactions reacted in the active period of the facultative bacteria, and acidification/degradation reactions reacted in the active period of the anaerobe, as shown in FIG. 7.

The reaction time of the aerobic retting reaction is based on the opening time of the valve C. The reaction time of the aerobic retting reaction increases with the opening time of the valve C. Therefore, the reaction time of the aeration agitation process can be determined by the volume and the concentration of the domestic sewage. In a preferred embodiment, the opening time of the valve C is one hour.

In the aerobic retting reaction, the bacteria that can not resist high temperature will decompose the degradable carbohydrate and fat in the organics, which are relatively easy to be decomposed, and release heat to rise the temperature simultaneously. The temperature will reach 15 to 40 degrees Celsius. Then the high temperature resistance bacteria will breed quickly. The protein and fiber that are hard to be degraded will be oxidized and decomposed under the aerobic conditions, and release large amounts of heat simultaneously, and the temperature will reach 60 to 70 degrees Celsius. When the organics are degraded substantially, the thermophilic bacteria will stop breeding because of the lack of nutrients, and therefore, the heat production will stop simultaneously. Then the temperature will drop and stay at 40 degrees Celsius, the retting reaction will be stable and form humus.

In the retting process, the retting reaction can react in an environmental temperature. In an exemplary embodiment, the environmental temperature is more than 35 degrees Celsius. An agitation process will shorten the retting time. In addition, the retting digestion tank can also be heated by a temperature control equipment. The heated temperature of 55 degrees Celsius is preferred. During the heating process, the temperature being heated from the environmental temperature to 55 degrees Celsius will cost about 1 day. The optimum temperature of the aerobic retting reaction of the aerobiont is 17 to 25 degrees Celsius, which corresponds to the temperature at the initial heating process. The main time of the retting reaction is the active period of the anaerobe after the retting reaction has reacted for one day, with a temperature reaching 55 degrees Celsius. When the temperature reaches 55 degrees Celsius, the temperature control equipment can be turned off automatically by a temperature control valve, and the remained retting reaction can keep reacting as a high-temperature fermentation reaction by the heat spontaneously generated by the retting reaction. The temperature can reach 70 degrees Celsius.

The gas produced in the retting reaction can flow into the gas tank via the check valve. In the retting process, the gas produced by the decomposition of the organics gathers together and has a certain pressure, and the check valves make sure the gas flows only in one direction from retting digestion tank to gas tank, and then to sewage gas generating tank. The sewage gas produced in the sewage gas generating tank is discharged to sewage gas appliances (e.g. methane boiler, methane generator). Therefore, the liquid pressure in the gas agitator of the sewage gas generating tank is 0.07 Mpa. The gas tank is designed as a cushion device, and the pressure of the gas tank is 0.07 Mpa to 0.1 Mpa.

The reaction time of the retting process can be determined by the volume and the concentration of the domestic sewage. In this embodiment, the reaction time of the anaerobe high-temperature reaction is 3 days.

In a preferred embodiment, the retting device includes at least three retting digestion tanks. Therefore, three different operation states can exist simultaneously, which can make the system keep running continuously when the retting reaction time is 2 to 3 days. The three different operation states are respectively retting state, material outputting state, and material inputting state. In one embodiment, there are three retting digestion tanks I, II, III connected in parallel with each other as shown in a aforementioned embodiment. In a particular embodiment, the retting digestion tank I is in the retting state; the retting digestion tank II is in the material outputting state, and the retting digestion tank III is in the material inputting state. The operational processes of the three retting digestion tanks are as follows:

The retting digestion tank I:

Closing the valves A1, B1, D1, E1, and F1.

Opening the valve C1, and then closing the valve C1 after an hour, the aeration agitation in the initial stage of the retting process will been completed.

Opening the valve G1, the heat medium source begins to heat, when the temperature reaches 55 degrees Celsius, the temperature control valve will close automatically, and then close the valve G1, the temperature can reach 70 degrees Celsius by the heat spontaneously generated by the retting reaction.

The retting digestion tank II:

Switching the state to an material outputting state.

Opening the valves E2, F2 (the valve E is a pressure balancing valve, balancing the gas flowing from the inputting material tank into the outputting material tank), and the retted liquid will be discharged.

The retting digestion tank III:

Switching the state to an material inputting state.

Closing the valve F3.

Opening the valves B3, D3, viewing the upper window, and when the liquid level reaches to a default level, closing the valves B3, D3.

Opening the valve A3, viewing the upper window, and when the liquid level reaches a default level, closing the valves A3, E3. The state of the retting digestion tank III can be switched to a retting state after the inputting material process finishes.

Gravel discharging: a gravel exit is defined at the bottom of each retting digestion tank. The gravel is discharged after the retting process, which changes the conventional way of sinking and discharging the gravel before the domestic sewage treatment. Therefore, the organism in the discharged gravel is very little, which is one reason of that the method of the present patent application will not cause secondary pollution.

In a conventional retting process, the switch of the three states is operated manually, and that causes the operation discontinuous. However, in the method of the present patent application, the upper clear liquid separated in the multi-phase separation process can be conveyed to the next process directly, and that makes the system operate continuously. In addition, the retting digestion tanks connected in parallel with each other improve the efficiency and make the operation more flexible, and solve the problem of anaerobic digestion requiring long time.

Figure 8:
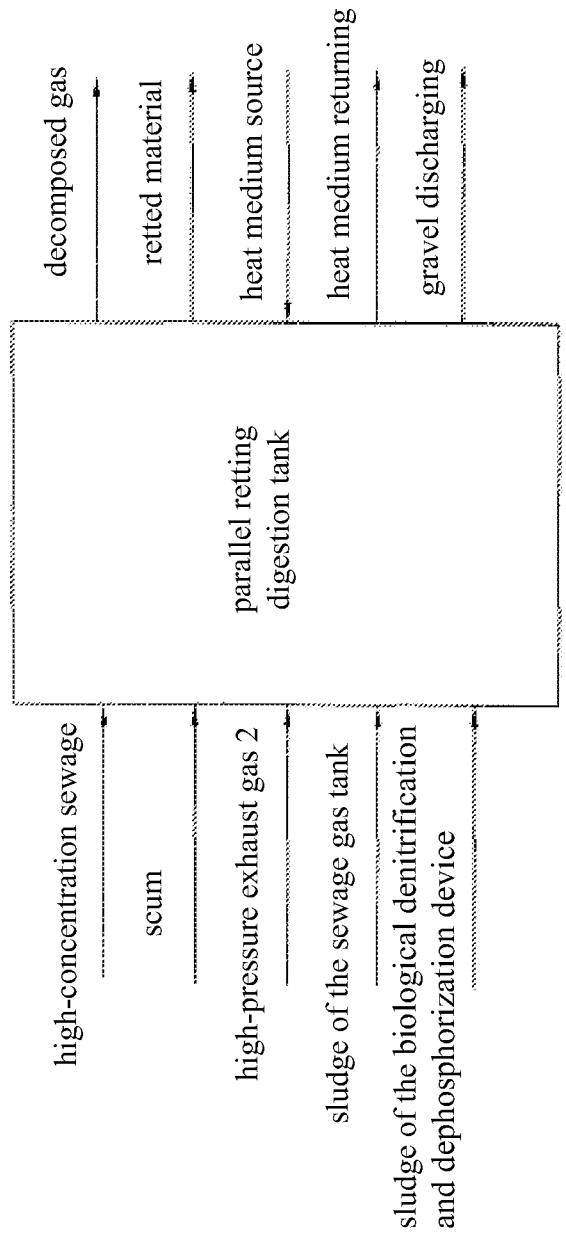
FIG. 8 is a block diagram of the retting digestion units connected in parallel with each other.

In the embodiments of the present patent application, the high-pressure exhaust gas 2 is used in an increased oxygen stir process at the initial stage of the retting process. In another embodiment, the scum and sludge produced in the sewage gas generating process, and the sludge produced in the optional biological denitrification and dephosphorization process can be conveyed to the retting digestion tanks to re-ret and will be retted into decomposed gas and retted material. The external source is used to heat at the initial stage of the retting reaction, and the heat generated in the retting reaction can help with the heat medium returning, as shown in FIG. 8.

3. Generating Sewage Gas Device

Figure 9:
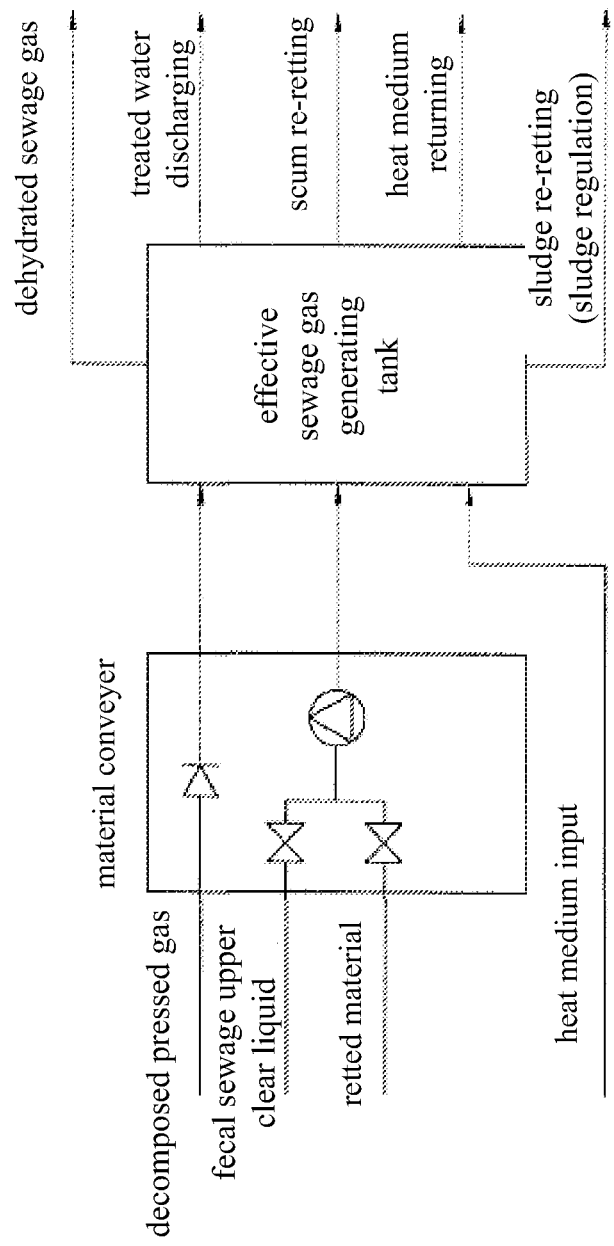
FIG. 9 is a flowchart of the process of generating sewage gas preformed by a high-efficiency sewage gas generating device.

The sewage gas generating device includes a material conveyer and sewage gas generating tank connected to the material conveyer in series as shown in FIG. 9, which runs automatically and continuously. The material conveyer includes a premixing device. The premixing device mixes the fecal sewage upper clear liquid separated by the multi-phase separation device and the retted material. The material conveyer further includes a decomposed pressed gas pipeline and defines a fecal sewage upper clear liquid entrance, a retted material entrance, and a mixed material exit. The sewage gas generating tank defines a decomposed pressed gas entrance, a mixed material entrance, a heat medium entrance, a dehydrated sewage gas entrance, a water exit, a scum re-retting exit, a heat medium returning exit, a sludge regulation exit and a sludge re-retting exit. The sludge regulation exit and the sludge re-retting exit can be defined at the same place.

Method

In the sewage gas generating process, the material conveyer mixes the fecal sewage upper clear liquid separated by the multi-phase separation device and the retted material according to the predetermined proportion. The mixed material is conveyed into the sewage gas generating tank by a centrifugal pump and is synthesized to form methane by the anaerobe. The retted material is a hydrolytic and acidifying original material for generating sewage gas. The fecal sewage upper clear liquid is original material liquid for generating sewage gas. The fecal sewage upper clear liquid is easily absorbed by the anaerobe. The proportion of the fecal sewage upper clear liquid and the retted material will not influence the organic load rate (OLR) of the sewage gas generating. In one embodiment, the volume of the retted material retted by one retting digestion tank is 25 m$^3$, while the volume of the upper clear liquid is about 80 m$^3$, and the proportion of them is about 1:3.2. The fecal sewage upper clear liquid has an effect on reducing the temperature of the retted material and diluting the concentration of the retted material. The fecal sewage upper clear liquid includes deliquescent carbohydrate, amino acid, monosaccharide, and so on, which are easily absorbed and digested by the anaerobe to synthesize methane and carbon dioxide. When the pressure of the decomposed pressed gas entrance exceeds the threshold of the liquid pressure in the sewage gas generating tank, the decomposed gas can get into the sewage gas generating tank via the check valve and the powerful gas agitator to achieve agitation. The decomposed gas mainly includes $H_2$, $CO_2$, $NH_3$, and $H_2S$.

The organic anaerobic digestion reaction and product in the sewage gas generating tank are as follows.

The biological catabolic and anabolic activities are continued:

anaerobe+deliquescent carbohydrate, amino acid, monosaccharide=organic acids+alcohols+$H_2$+$CO_2$+$NH_3$+energy (Biological decomposition reaction)

anaerobe+organic acids=new biological cell (Biosynthetic reaction)

The methane is synthesized by the alcohols and $CO_2$:

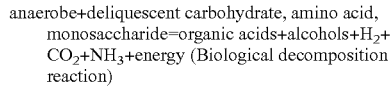

$4CH_3COOH \rightarrow CO_2+H_2O+3CH_4$

The methane is synthesized by the volatile acid:

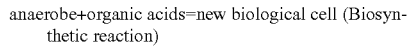

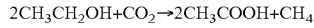

The methane is synthesized by the hydrogen reduction of the carbon dioxide:

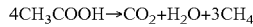

The temperature is one of the important factors affecting the anaerobic digestion. The temperature affects the biochemical reaction speed, and therefore, it relates to the decomposition rate of the organics. The middle digestion temperature is 30 to 38 degrees Celsius (33 to 35 degrees Celsius is preferred); the high digestion temperature is 50 to 55 degrees Celsius. In this embodiment, the sewage gas generating reaction is reacted at a temperature of 35 degrees Celsius. The anaerobic digestion needs a stable temperature, for example, the variation per day is less than ±2 degrees Celsius. If the variation changed significantly, the system may stop producing gas. In this embodiment, the way of keeping a constant temperature is using a heat medium circulation device and controlling the temperature by an temperature control device automatically. The control accuracy is within ±1 degree Celsius.

The sewage gas can be discharged after been dehydrated by an expansion condensing dehydrator. The water dehydrated from the sewage gas can flow into the denitrification and dephosphorization device automatically of the next step.

The sewage gas generating tank can work automatically and continuously, because the pollutants has been degraded in the foregoing retting process, the sewage gas generating tank is capable of withstanding great hydraulic load. The organics in the water dehydrated from the sewage gas is very little, and the sewage gas production rate is also improved.

According to a book *Sewage Gas Technology and Application*, published by the Chemical Industry Press, the sewage gas production rate of the feces biogas digester is 0.28 m$^3$/m$^3$·d. In one embodiment, the inputting original materials are the pre-treated and pre-reacted fecal sewage upper clear liquid and retted material, and the mixed original materials are diluted liquid. The average daily volume of the mixed original materials is 850 m$^3$, the average daily production of the sewage gas is 260 m$^3$, and the effective volume of the sewage gas generating tank is 30 m$^3$. The sewage gas production rate is 0.3 m$^3$/m$^3$·d calculated according to the volume of the inputting materials. The sewage gas production rate is 8.6 m$^3$/m$^3$·d calculated according to the effective volume of the sewage gas generating tank.

Re-retting

Scum re-retting: most of the pollutants that are not indigested easily or are digested with long time will form scum in the sewage gas generating tank. If those pollutants are discharged and re-retted timely, the sewage gas production condition will be improved, and the indigested pollutants can be digested repeatedly until digested completely. The re-retting process is achieved inside of the system.

Biological sludge re-retting: all the sludge remained in the sewage gas generating tank are conveyed back to the retting process to re-ret. On one hand, the returned sludge can supply enough amounts of living things that the retting reaction requires, on the other hand, the returned sludge can create a self-domesticated environment to the anaerobe, which makes the living things in the sewage gas generating tank mainly be methane bacteria, and a short lifetime of bacteria may improve the sewage gas production rate. The aerobiont has strong absorption, oxidation, and hydrolysis abilities; therefore, if the aeration sludge and the aeration agitation process are added in initial stage of the retting reaction, the absorption, oxidation, and hydrolysis can be accelerated in the initial stage of the retting reaction. When retting reaction becomes to an anaerobic reaction, the added anaerobic sludge can help the domestic sewage be acidized and degraded rapidly. The aerobiont and the anaerobe provide nutrient and environment to each other during the re-retting process, and both of them can be digested and domesticated, therefore, the total amounts of the discharged sludge can be reduced.

Bottom Sediment and Bottom Liquid Returning

In another embodiment, the bottom sediment and the bottom liquid can be conveyed back to the pretreatment tank by the Nikuni pump, and can achieve an anaerobic sludge adjustment to the domestic sewage, and that will improve the separation effect of the pretreatment. The bottom sediment and the bottom liquid will subside and become a part of the sediment liquid, and then they will be conveyed into the retting device to be re-retted.

Figure 10:
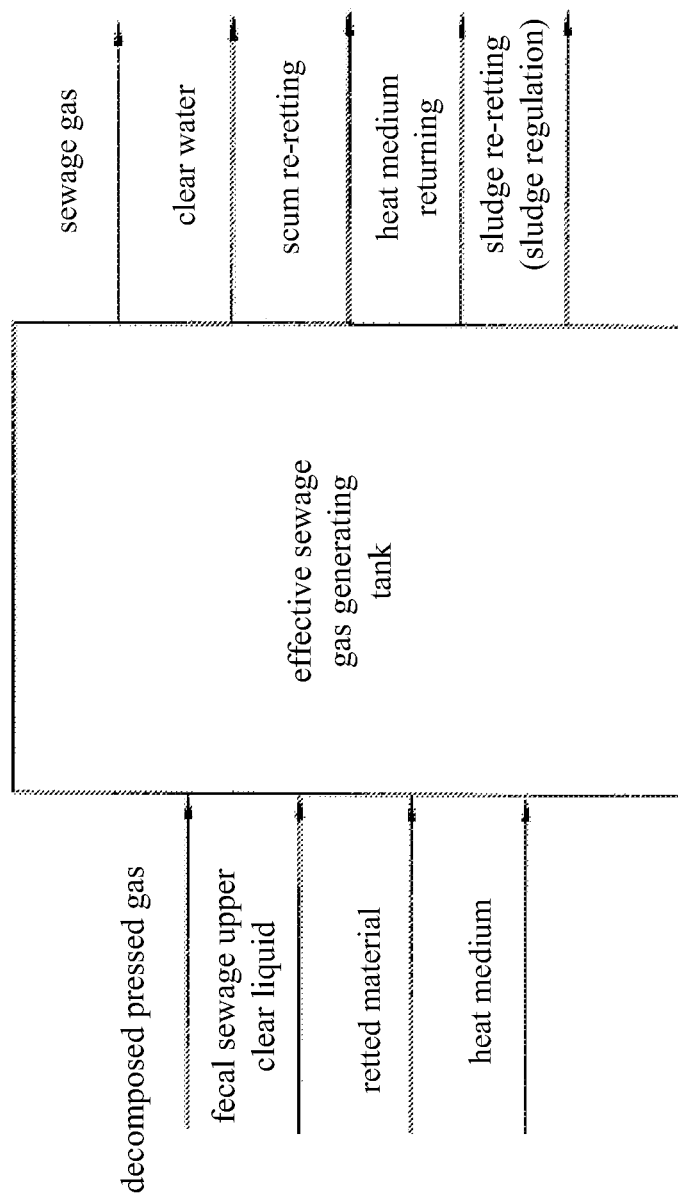
FIG. 10 is a block diagram of the high-efficiency sewage gas generating device.

During the sewage gas generating process, the retted decomposed gas is used to an aeration agitation process, and the retted material and the fecal sewage upper clear liquid separated by the multi-phase separation device are synthesized to dehydrated sewage gas and treated water of the sewage gas tank. The scum and the sludge are re-retted. The heat medium source are used in the sewage gas generating process, and the heat generated in the sewage gas generating process can be reused, as shown in FIG. 10.

4. Biological Denitrification and Dephosphorization Device

Figure 11:
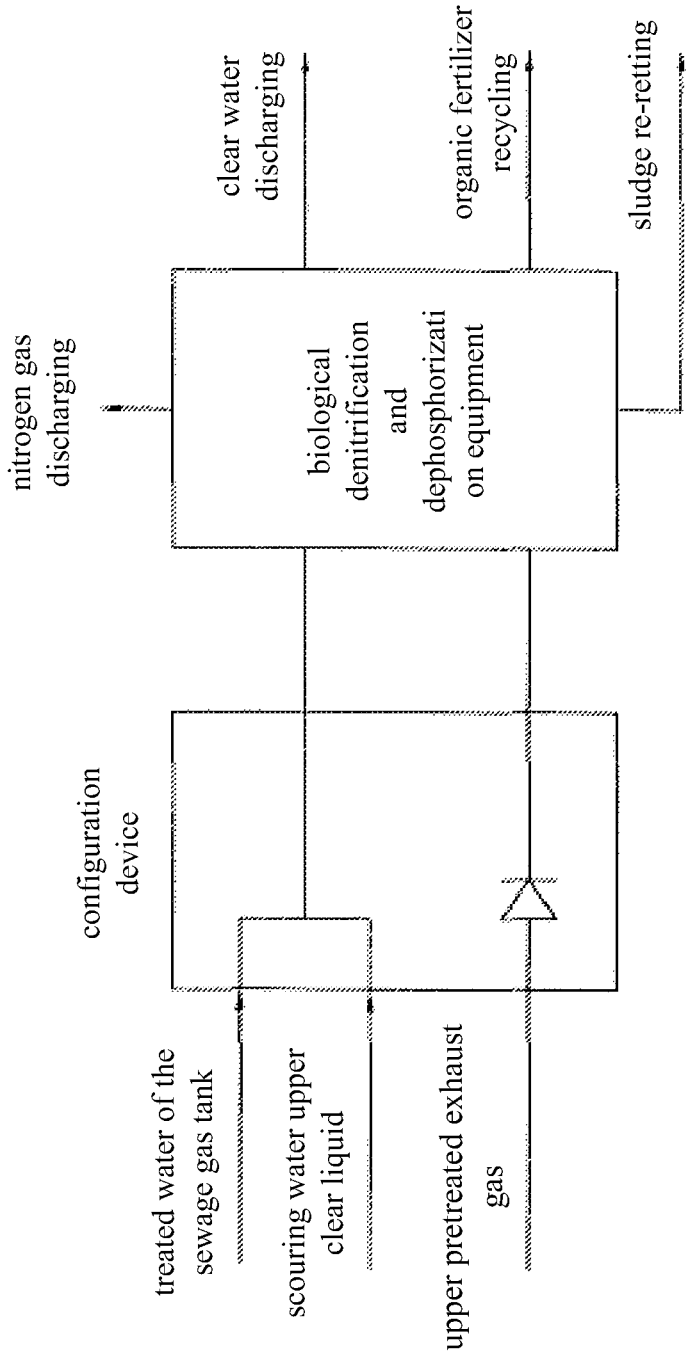
FIG. 11 is a flowchart of the process of biological denitrification and dephosphorization preformed by a biological denitrification and dephosphorization device.

Referring to FIG. 11, the biological denitrification and dephosphorization device includes a configuration device and a biological denitrification and dephosphorization equipment. The configuration device includes a premixing device mixing the scouring water separated by the multi-phase separation device and the treated water of the sewage gas tank. The configuration device further includes a passage conveying the high-pressure exhaust gas 1 and defines a sewage gas tank treated water entrance, a scouring water upper clear liquid entrance, a high-pressure exhaust gas 1 entrance, a mixed liquid entrance and an upper pretreated exhaust gas exit. The biological denitrification and dephosphorization equipment includes at least one tank. If the number of the tank is more than one, the at least two tanks are connected with each other in series, for example, the tank 1 and tank 2. Each tank defines a mixed liquid entrance, a high-pressure exhaust gas 1 entrance, a nitrogen gas discharging exit, a clear water discharging exit, an organic fertilizer recycling exit and a sludge re-retting exit.

In one embodiment, the biological denitrification and dephosphorization equipment includes a tank 1 and a tank 2. The tank 1 includes three chambers separated perpendicularly by two clapboards. The three chambers are plankton chamber, biofilm chamber and initial settlement decanted chamber.

The volume of the plankton chamber is 15 m$^3$, including a plurality of cube foams, the dimension of each cube foam is 1 cm×1 cm×1 cm, and the total cubage of the cube foams is 5 m$^3$. The bottom of the plankton chamber is mounted a powerful gas agitator communicated with the bottom of the biofilm chamber. The top of the plankton chamber is communicated with the device discharged denitrification gas. The denitrification gas is discharged by a vent pipe. The cube foams are carriers of the aerobiont in the plankton chamber, which will improve the concentration of the planktons observably. The concentration of the planktons is about 20 to 35 g/L, which is 8 to 10 times higher than that of the scattered planktons. The powerful gas agitator can agitate the planktons to make sure the planktons can contact with the liquid adequately and obtain more dissolved oxygen, so as to improve the efficiency of the biological treatment.

The secondary deposition tank is one component of the optional biological denitrification and dephosphorization equipment. The discharged water of the optional biological denitrification and dephosphorization tank includes certain amount of SS and floating sludge which needed to be settled again to meet the A level drainage standard of China.

In one embodiment, the secondary deposition tank has a same structure as the biological denitrification and dephosphorization tank. There are two clapboards in the secondary deposition tank to form two deposition chambers and an ascension chamber. The ascension chamber is located between the two deposition chambers, and the deposition chambers are communicated with the bottom of the ascension chamber. The area of the ascension chamber is 4 times larger than that of the deposition chamber. Each deposition chamber defines one water entrance communicated with the water exits of the biological denitrification and dephosphorization tank. The top of the ascension chamber has a water exit to discharge the deposited water. When the water flow down to the bottom from the two water entrances of the deposition chamber, the two gushes of water will combine together and flow up to the ascension chamber. The rate of the up-flowing water is become half of the rate of the down-flowing water ($V_{up}=\frac{1}{2}V_{down}$), the rate of the up-flowing water is slow, and that may help the deposition. The up-flowing water is separated into sludge and clear water by an inverted semicircular-shaped sludge resisting board. The clear water will keep flowing up form the interspace of the sludge resisting board and the sludge will drop down to the bottom. If the depth is more than 4.5 m, the separation effective will be improved significantly. The sludge can drop down to the bottom via the inner arc face of the sludge resisting board. The secondary deposition tank has an exit to discharge the bottom sludge and the bottom liquid by a pump. The total amount of the discharged bottom sludge and liquid is $\frac{1}{10}$ of the total volume of the secondary deposition tank. The bottom sludge and the bottom liquid are mixed with the sewage gas liquid discharged by the sewage gas generating tank, then the mixed material are conveyed back into the biological denitrification and dephosphorization tank to be retreated. There are two gushes water with different flowing orientations and different flowing rates at the bottom of the secondary deposition tank. In one embodiment, the cross-sectional area of the ascension chamber is 1.9 m$^2$, and the amount of the water of the ascension chamber $Q_{up}=Q-\frac{1}{10}Q$, the flowing rate $V_{up}=Q\times\frac{9}{10}\times1/1.9=0.47Q$; the cross-sectional area of the bottom exit DN50 is 0.002 m$^2$, the discharging rate of the pump $Q_{pump}=\frac{1}{10}Q$, the flowing rate $V_{pump}=Q\times\frac{1}{10}\times1/0.002=50Q$. It is obvious that the two flowing rates have a hundredfold difference, therefore, a new separation and deposition method is designed. The specific gravity of the sludge is larger than that of the clear water, therefore, the sludge will flow with a orientation the same as the flow with a high flowing rate and be discharged. The method of secondary deposition has no requirement to the stay time of the water, which reduces the occupied area of the secondary deposition equipment. Meanwhile, this method also solves the problem in the secondary deposition the phosphorus enrichment bacteria having long staying time and releasing phosphorus again because of hypoxia.

Method

After the sewage gas tank treated water and the scouring water upper clear liquid have been mixed by the premixing device of the configuration device, the mixed material will be conveyed into the biological denitrification and dephosphorization equipment. The high-pressure exhaust gas 1 separated by the multi-phase separation device is used in an aerobic mixing of the nitrogen removal treatment.

The treated water is conveyed into the plankton chamber from the upper entrance, and flows up into the biofilm chamber. The bottom of the plankton chamber is also mounted a powerful gas agitator. The water flow including microbubbles created by the powerful gas agitator can only flow up because of the resistant by the biofilm carrier. The surface of the biofilm carrier forms water flow to provide oxygen to the biofilm. The water flow including micro-bubbles can make the biofilm drop and be discharged from the upside, so as to improve the metabolic environment and permit the interspace of the biofilm carriers reducing to 10 mm. The biofilm carrier is produced by the nylon and mounted perpendicularly in an assembly box. The box can be mounted in the tank, the effective contacting area of the surface of the biofilm and the liquid can reach 1800 m$^2$, and the biological concentration can reach 250 to 300 g/L, and there will be no obstruction in the treatment. The aerobic reaction mainly depends on the organisms of the biofilm contacting with the liquid, the organisms inside of the biofilm can be ignored. According to the above parameters, in one embodiment with treating 2000 tons of domestic sewage per day, the two powerful gas agitators consume gas quantity 1.5 m$^3$ per hour, and the measured residual amount of the dissolved oxygen is more than 1 ppm (parts per million).

The optimum temperature of the aerobic reaction of the biological denitrification and dephosphorization is 17 to 25 degrees Celsius. The temperature of the treated water discharged by the sewage gas generating tank is 35 degrees Celsius, mixed with the scouring water upper clear liquid with a proportion 1:1.5. The variation of the temperature of the scouring water upper clear liquid relates to the environment temperature, about 9 to 20 degrees Celsius. Therefore, the temperature of the mixed liquid is about 19 to 26 degrees Celsius. The gas stir can reduce the temperature of the mixed liquid, and that will make the temperature fit with the optimum temperature of the biological denitrification and dephosphorization reaction.

The water treated in the biofilm chamber overflows from the upside of the biofilm chamber and enters the initial settlement decanted chamber. The indigested organic biological sludge settles to the bottom of the initial settlement decanted chamber, the clear water is decanted by a tooth-shaped structure and enters the secondary deposition tank. The clear water is deposited again and is discharged to outside from the system.

The remained biological sludge in the tank 2 is conveyed back into the retting tank. On one hand, the returned sludge can supply enough living things that the retting reaction requires, on the other hand, the returned sludge can take the absorbed organics back into the retting tank, which reduces the stay time of the domestic sewage in the biological denitrification and dephosphorization process and the secondary deposition process. The chemical oxygen demand (CODcr) of the discharged water is not more than 50 mg/L, and the biochemical oxygen demand (BODs) of the discharged water is not more than 5 mg/L. The anaerobe in the biological denitrification and dephosphorization tank mainly includes facultative denitrification bacteria and aerobic polyphosphate bacteria. The denitrification bacteria can be used to reduce the nitrate nitrogen to remove the nitrogen. The aerobic polyphosphate bacteria can oxidize the self-carbon to store the poly-β-hybroxybutyric acid and obtain energy from some simple organisms (e.g. acetic acid) and phosphate in the domestic sewage. The phosphorus can be removed by discharging the sludge in the domestic sewage.

After a new system is installed, the aerobic sludge can be collected from the working system to breed for the biological denitrification and dephosphorization device. After breeding, the discharged water can be conveyed to the water entrance of the biological denitrification and dephosphorization device to be recycled. During the working process, gas agitation is needed to increase the oxygen, the domestic sewage is conveyed into the system gradually and the clear water is discharged to culture and develop biofilm. After 10 to 15 days, the domestic sewage is injected into the sewage gas generating tank, and the sewage gas generating tank is bred by the sludge produced in the biological denitrification and dephosphorization process. The sewage gas generating tank can be turned on a normal state after been closed 5 days. Because of the self-domestication, variation, propagation of the biological material, the system can work normally after 2 to 3 months.

Figure 12:
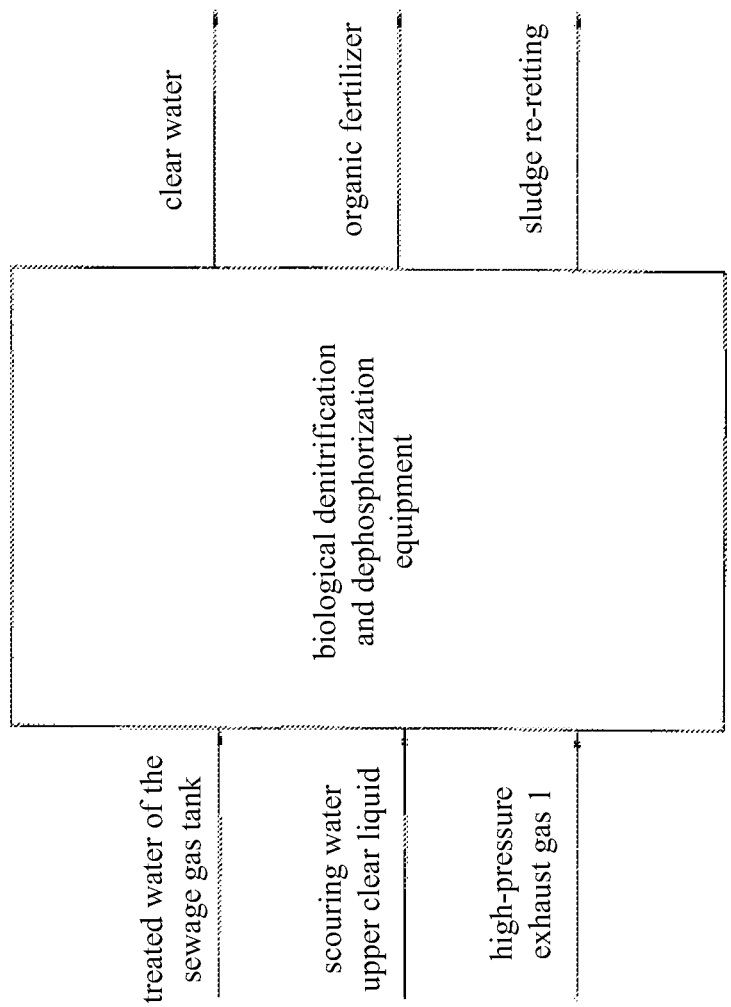
FIG. 12 is a block diagram of the biological denitrification and dephosphorization device.

The sewage gas tank treated water and the scouring water upper clear liquid can be purified into clear water, organic manure and nitrogen gas, as shown in FIG. 12.

Re-retting

The aerobiont has strong adsorption ability; therefore, the sludge includes a large amount of aerobiont. Most parts of the sludge are re-retted, supplying sufficient amount of living things what the initial retting reaction needed and accelerating the absorption efficiency. The polyphosphate biological material carrying phosphate is being recycled in the system to be combined with heavy metal ions and poisonous elements and take these pollutants out of the system. The method of re-retting the aerobiont is effective, and reduces the quantity of the sludge. The recycling of the phosphorus can clear the poisonous and hazardous substances.

Bottom Sediment Returning

Figure 17:
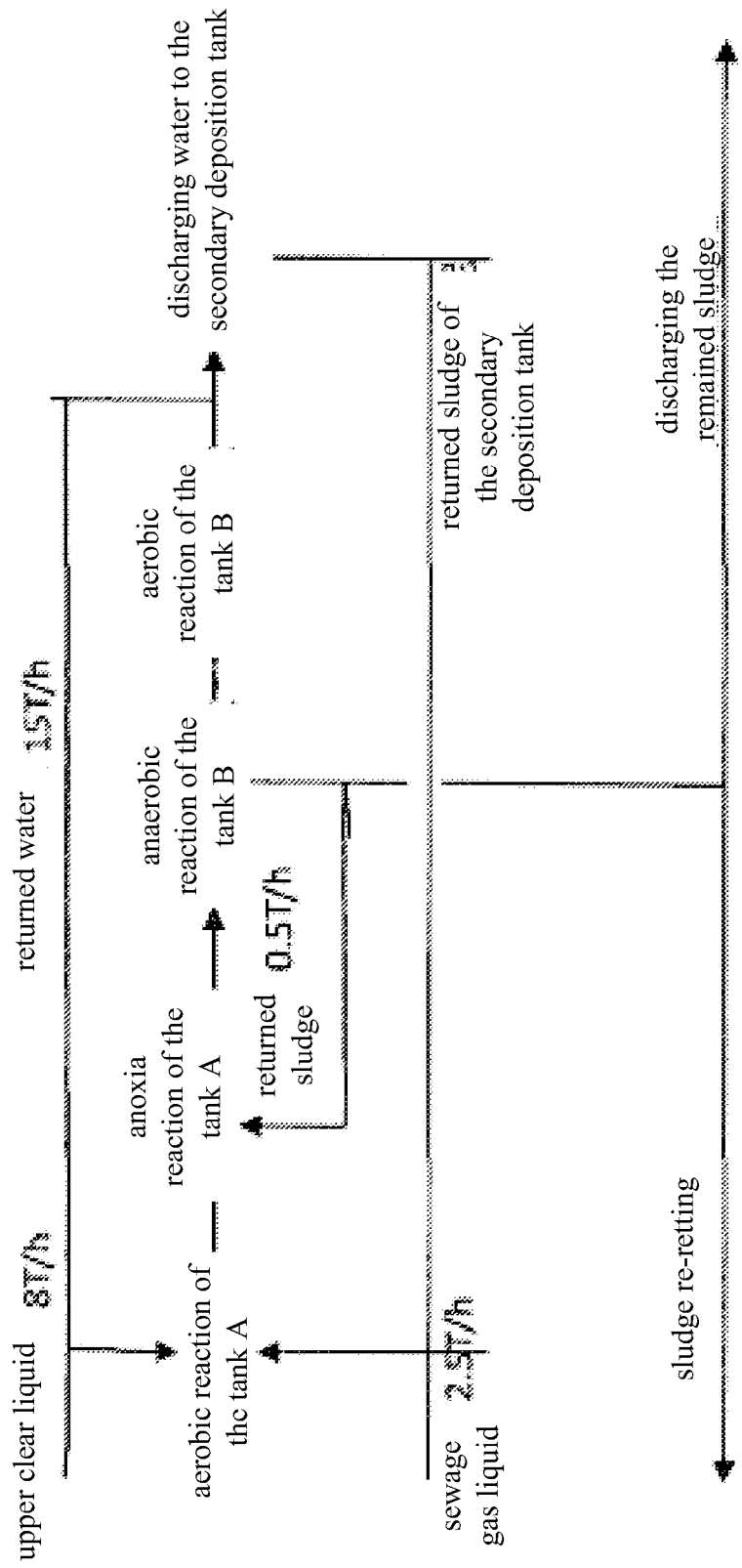
FIG. 17 is a flowchart of the process of biological denitrification and dephosphorization preformed by two biological denitrification and dephosphorization tanks connected in series.

During the biological denitrification and dephosphorization process, two tanks (tank A and tank B) are connected in series and form an OAAO circulation treatment process (including a prepositive aerobic biological treatment process, a facultative biological treatment process and a postpositive anaerobic aerobic biological treatment process, abbreviate to OAAO, as shown in FIG. 17). The water flow carrying sludge can take the sludge in the tank A into the tank B. On one hand, a plurality of nitrifying bacteria are taken into the aerobic reaction of the tank B to prevent the normal action of the polyphosphate bacteria, commonly known as nitrification, denitrification, phosphate release and polyphosphate to snatch carbon source. On the other hand, if the sludge is discharged form the tank B to remove the phosphorus, however, a substantial amount of nitrifying bacteria and denitrifying bacteria will be discharged together. Therefore, in this method, the bottom sludge and the bottom liquid in the tank B will be conveyed back into the tank A. In one embodiment, if the amount of the returned sludge is 0.5 T/h, the amount of the nitrogen in the discharged water can be zero, and the amount of the phosphorus in the discharged water is also decreased. This means that the different kinds of bacteria can have different functions when they are at different places. The sludge in the tank A can help denitrifying bacteria remove nitrogen under an anoxic environment. The polyphosphate bacteria can be recycled into the aerobic reaction and the anaerobic reaction of the tank B repeatedly, to achieve phosphate release and phosphate polymerization, so as to improve the effect of the phosphorus removal.

Embodiments

It should be understood that, although the present patent application has been specifically described on the basis of the following embodiments thereof, the present patent application will not be limited herein.

Address Picking for Experiment of Treating Domestic Sewage and Organic Garbage, Domestic Sewage Sources, Experiment System, and Etc.

The experiment address of the method and system for treating domestic sewage and organic garbage is No. 1918, TingFeng Road, TingLin Town, JinShan District, ShangHai City. The domestic sewage sources are the domestic sewage from the nearby residents, including the domestic sewage discharged from the canteen and the septic tank. The discharging rate of the domestic sewage is 200 to 250 T/d. The domestic sewage has the characteristics of high COD, high T/P and high SS. The treatment capacity of the experiment equipment is 300 T/d. The experiment system is designed with a reduced size. The diameter of the tank is 2.2 m, and the occupied area of the tank is 17 m×8 m. The equipments of the system are shown in the following table 1.

TABLE 1

| Equipment name | Main auxiliary parts | Quantity |
|---|---|---|
| Multi-phase separation pretreatment device | Pretreatment tank 2#A, gravel extracting machine, auto-separating grating machine, upper clear liquid regulation tank, ascending pump, organic garbage crushed, material inputting ascending funnel, roots blower, and sludge agitation adjustment device | 1 |
| Parallel retting digestion tanks | Insulation retting digestion tank 3#A-3#D, automatic control box, pneumatic control device, inputting pump, agitation pump, outputting pump, head valve | 4 |
| Effective sewage gas generating device | Effective sewage gas generating tank, feeding monitoring device, sewage gas meter, and heat exchanger | 2 |
| Denitrification and dephosphorization device | Denitrification and dephosphorization tank 5#A and 6#A, secondary deposition tank6#, and sludge discharged device | 1 |

According to the method of the present patent application, the above equipments are used to treat the domestic sewage and organic garbage, and the test results are described in the following 1 to 4 embodiments.

Embodiment 1 is an experiment to test the separation capacity of the multi-phase separation pretreatment device.

The domestic sewage sources are separated by the multi-phase separation pretreatment device according to the method of the present patent application. The parameters of the original domestic sewage are shown in the following table 2 (T/N is the abbreviation of the total nitrogen pollutants, in units of mg/L):

TABLE 2

| pH | COD | T/N | T/P | SS | DO |
|---|---|---|---|---|---|
| 6.90 | 1008 | 16.77 | 19.75 | 401 | 3.67 |

The inflow rate of the domestic sewage is 7.5 T/h, and the returning rate of the anaerobe bottom sludge and the bottom liquid from the sewage gas generating device is 0.5 T/h. The domestic sewage flowing into the upper floating chamber is agitated with the sludge. The samplings of the upper clear liquid, the upper floating liquid and the sediment liquid are tested to obtain related data shown in the following table 3. The upper floating liquid and the sediment liquid are mixed to mixed liquid, and the parameters of the mixed liquid are shown in the following table 4.

TABLE 3

|  | pH | COD | T/N | T/P | SS |
|---|---|---|---|---|---|
| Upper clear liquid | 7.45 | 199 | 15.60 | 11.20 | 160 |
| Upper floating liquid | 7.66 | 13830 | 63.00 | 164.55 | 22987 |
| Sediment liquid | 7.64 | 46440 | 443.00 | 327.30 | 66160 |

TABLE 4

| pH | COD | T/N | T/P | SS |
|---|---|---|---|---|
| 7.65 | 30135 | 253 | 246 | 44574 |

Figure 13:
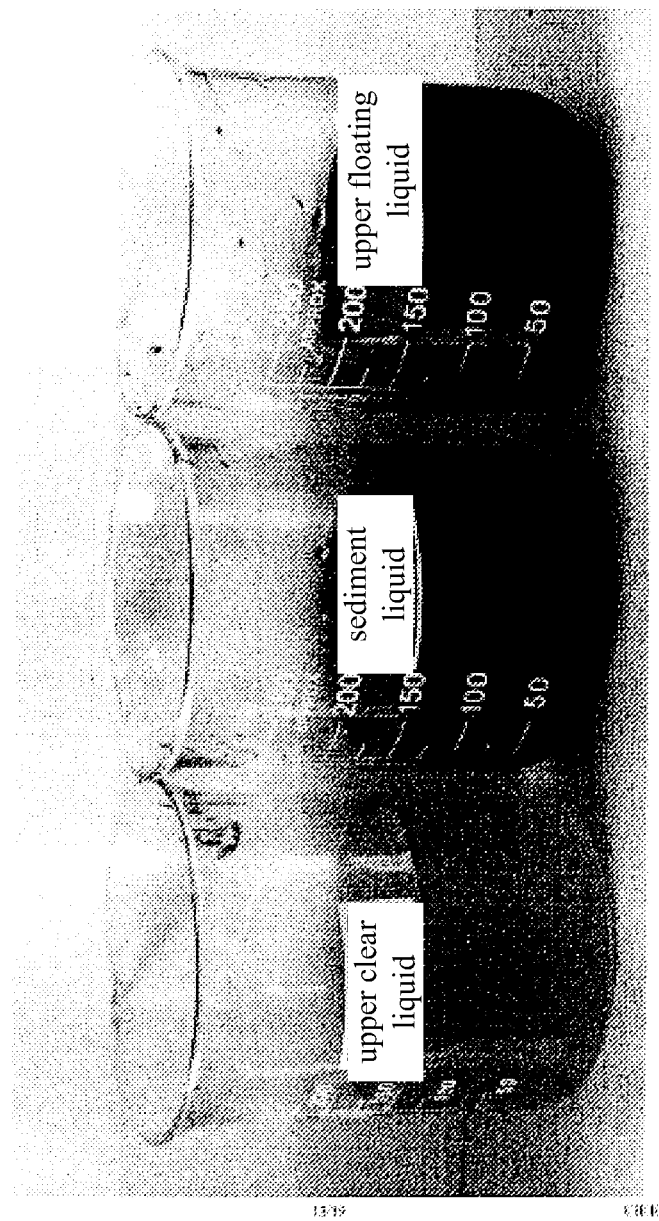
FIG. 13 is a perspective view of separated samplings of upper clear liquid, upper floating liquid and sediment liquid.
Figure 14:
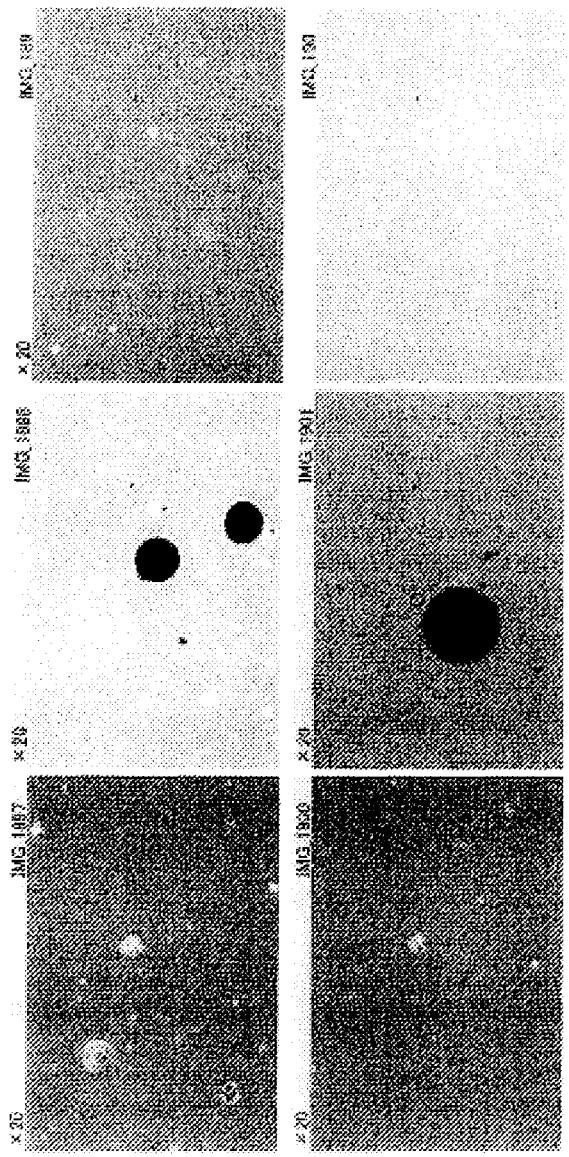
FIG. 14 is a micrograph of the upper clear liquid.
Figure 15:
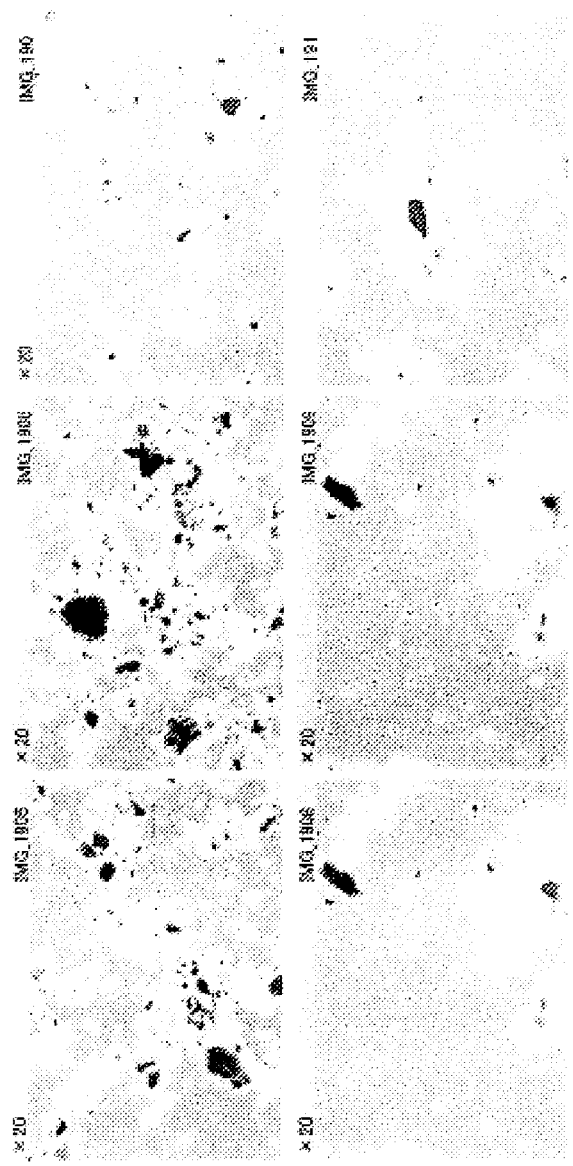
FIG. 15 is a micrograph of the upper floating liquid.
Figure 16:
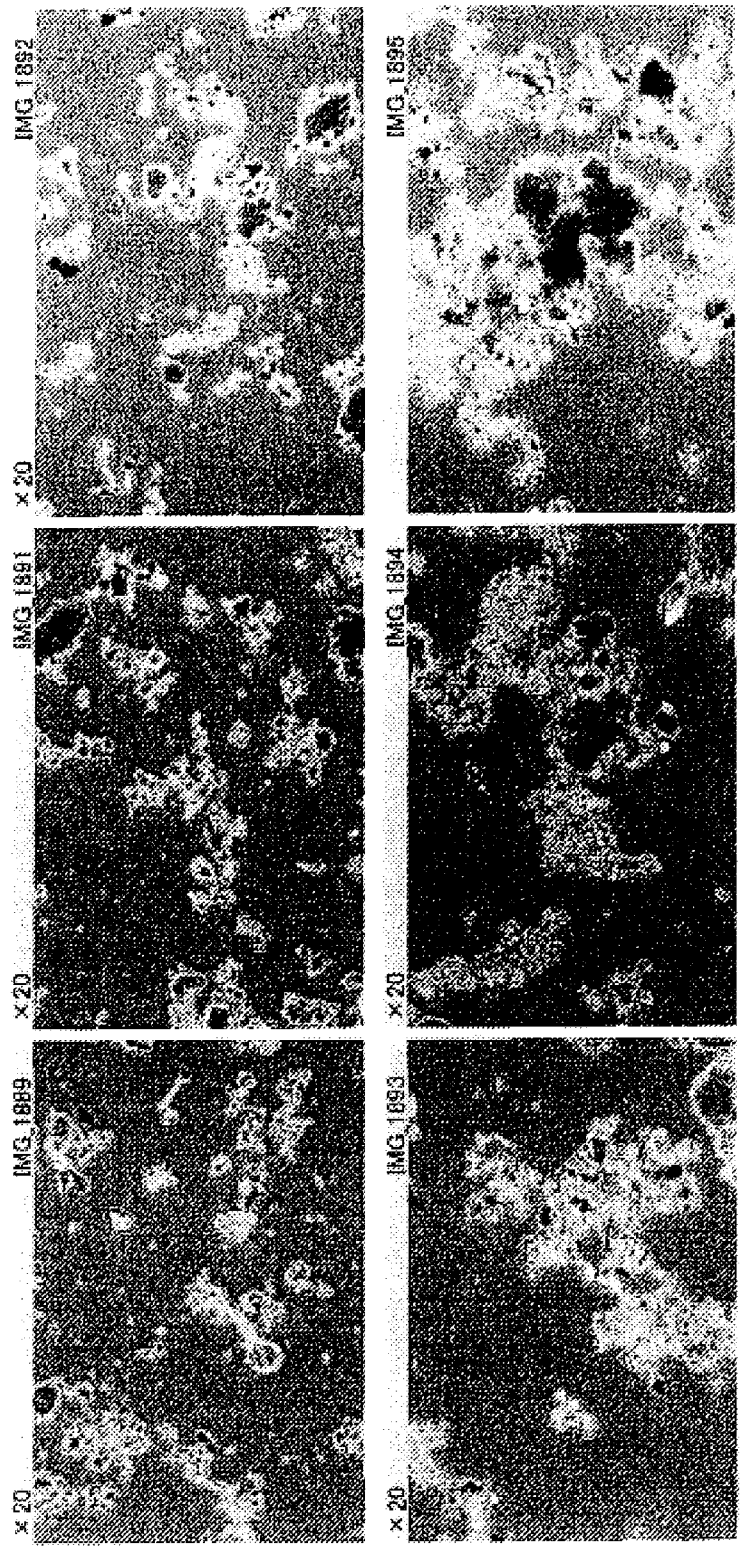
FIG. 16 is a micrograph of the sediment liquid.

When observing the samplings of the liquid liquid-phase separated by the multi-phase separation pretreatment device with the unaided eye, the sampling of the upper clear liquid is light-colored and clear, and the samplings of the upper floating liquid and the sediment liquid are obviously in a high-concentration state, as shown in FIG. 13. When observing the sampling of the upper clear liquid with a microscope, some spherical oil droplets are found. The dispersed oil pollutants in the micrograph are spherical, and the person skilled in the art can distinguish that the oil pollutants are nitrogenous pollutants, commonly known as N pollutants. The average value of the T/N of the original domestic sewage is 16.77 mg/ml, and the average value of the T/N of the separated upper clear liquid is 15.60 mg/ml. The separation effect to the N pollutants is not obvious. In the micrograph of the sediment liquid, the anaerobic sludge absorbing the pollutants are sediment and gather together, which shows that the absorption and settlement of the returned anaerobic sludge that is pretreated can improve the separation (shown in FIGS. 14 to 16).

If the amount of the mixed liquid is set as a, and the amount of the upper clear liquid is set as b, that is, and the total amount of water equals a+b. The relationships of the amount of water are shown in the following table 5. It is suitable that the value of a is 5 percent less than that of (a+b).

TABLE 5

|  | Corresponding relationship | a/b |
|---|---|---|
| Estimated by COD | 108(a + b) = 30135a + 199b | 2.8% |
| Estimated by T/N | 16.77(a + b) = 253a + 15.6b | 0.5% |
| Estimated by T/P | 19.75(a + b) = 246a + 11.2b | 3.8% |
| Estimated by SS | 401(a + b) = 44574a + 160b | 0.6% |

The separation capabilities analyzed according to the parameters of the original domestic sewage and the upper clear liquid are shown in the following table 6.

TABLE 6

|  | COD | T/N | T/P | SS |
|---|---|---|---|---|
| Original domestic sewage | 1008 | 16.77 | 19.75 | 401 |
| Upper clear liquid | 199 | 15.60 | 11.20 | 160 |
| Separation capability | 80% | 7% | 43% | 60% |

The upper clear liquid regulation tank is added in the system to solve the problem of unstable water supply. The volume of the upper clear liquid regulation tank is 25 cubic meters. The storage of the upper clear liquid regulation tank at peak is 3 times larger than the average water amount, and supplies the stored water when the water supply is at a valley value. The adjustment time can last 4 hours to meet the system requirement.

The multi-phase separation device has the following advantages:

a. after the original domestic sewage is separated by the multi-phase separation device, 80% COD, 60% SS, 40% P pollutants in the original domestic sewage are gathered in the mixed liquid that is 5% of the total amount of water to form high-concentration sewage, so as to meet the requirements of the following different treatment methods. The separation effect to the N pollutants is not obvious in the pretreatment equipment.

b. because the gravel separation has a good designed structure, there is no gravel in the sediment liquid.

c. the irregular-shaped grating can reduce the size of the auto-separating grating machine, therefore, the power consumption of auto-separating grating machine is only 0.75 KW.

d. the exhaust gas produced by the multi-phase separation device can be discharged by the roots blower, so as to avoid peculiar smell giving off from the system and have obvious effect.

e. the crushing capability of the organic garbage crusher can reach 250 Kg/h, and all of the crushed organic garbage can pass through the filter with 80 meshes.

Embodiment 2 is an experiment to test the capacity of the parallel retting digestion devices.

The parallel retting digestion devices include four parallel retting digestion tanks. Each retting digestion tank includes an automatic control box to achieve controlling the inputting material, outputting material, agitating hydraulically, retting and heating automatically. The four retting digestion tanks are used one inputting pump by switching automatically. Each retting digestion tank includes an agitation pump and an outputting pump. Both the agitation pump and the outputting pump are screw pumps, with a flow rate of 2.5 T/h and a lift of 15 m. The inputting time and outputting time of each retting digestion tank are 14 hours, and the retting reaction of each retting digestion tank is also 14 hours. The inputting and the outputting are continuously corresponding to the retting process.

The organic garbage is inputted into the retting digestion tank by the crusher with a rate of 20 Kg/h. The tested parameters of the inputting material liquid are tested, and the parameters of the outputting material liquid will be tested after 20 hours. The removed amounts of a variety of parameters after the retting processing are shown in the following table 7.

TABLE 7

|  | COD | T/N | T/P | SS | Temperature | pH | DO |
|---|---|---|---|---|---|---|---|
| Input material |  |  |  |  |  |  |  |
| Tank 3#A | 37256 | 1688 | 189 | 45006 | 28.5 | 7.23 | 3.2 |
| Tank 3#B | 29008 | 1555 | 193 | 48799 | 30.0 | 7.46 | 4.1 |
| Tank 3#C | 40110 | 2317 | 206 | 43000 | 30.0 | 7.70 | 4.3 |
| Tank 3#D | 49879 | 2109 | 232 | 51064 | 29.5 | 7.68 | 4.2 |
| Average | 39063 | 1917 | 205 | 46967 | 29.5 | 7.52 | 3.95 |
| Output material |  |  |  |  |  |  |  |
| Tank 3#A | 1989 | 377 | 111 | 1220 | 40 | 6.95 | 0.40 |
| Tank 3#B | 1886 | 468 | 194 | 1214 | 40 | 6.80 | 0.20 |
| Tank 3#C | 1968 | 373 | 189 | 1188 | 41 | 6.78 | 0.16 |
| Tank 3#D | 2045 | 345 | 167 | 1168 | 41.5 | 6.65 | 0.16 |
| Average | 1972 | 391 | 165 | 1198 | 41.5 | 6.80 | 0.23 |

TABLE 8

Average removal rate

|  | COD | T/N | T/P | SS |
|---|---|---|---|---|
| Average of inputting material | 39063 | 1917 | 205 | 46967 |
| Average of outputting material | 1972 | 391 | 165 | 1198 |
| average removal rate | 95% | 79% | 20% | 97.5% |

TABLE 9

The daily retting decomposition capability N is calculated according to the inflow of 2.5 T/h, and the formula is: N = (average of input material − average of output material) × 60 T

|  | COD | T/N | T/P | SS |
|---|---|---|---|---|
| Average Unit Processing Value | 37091 | 1526 | 40 | 45769 |
| N Value | 2220 Kg | 91 Kg | 2.4 Kg | 2740 Kg |

According to the removal rate showing in table 8, the retting device has a strong degradation effect on the SS and COD, and it also has hydrolysis and acidification effects on the organic garbage, such as fat and protein. Therefore, the process design and the device design are successful.

The retting device has little effect on removing the phosphorus, and only 20% of phosphorus can be absorbed by the living things as nutrient, and the remained phosphorus are discharged into the water or stay in the water with a form of phosphate. Therefore, the output liquid needs to be further analyzed to research on an effective way of removing the phosphorus in retting processing so as to reduce the pressure of dephosphorization in the proceeding processing.

The flow rate of the agitation pump is 2.5 T/h, and the lift is 15 m.

The method for testing the retting time is as follows:

If the retting device is not heated and agitated, the temperature will rise after the retting reaction has reacted 16 hours, and the temperature will stop rise when it reaches 38 to 40 degrees Celsius. The rising time of the temperature is about 8.5 hours, and the retting reaction will cost 1 day. If the retting device is not heated but agitated when inputting material, the temperature will rise when the inputting begins. The temperature will reach 40 to 42 degrees Celsius after 4 hours later, even if the inputting has not finished. The retting reaction will cost 8 hours. If the retting device is heated but not agitated, the temperature will reach 36 degrees Celsius after 7 hours heating, and the temperature rises from 36 to 40 degrees Celsius by heat generated by the reaction will cost 4 hours. The above experiments show that the retting reaction time will be reduced to 8 hours by hydraulic agitation. Using the method of hydraulic agitation is very advantageous in the retting processing. However, the temperature of retting solely relying on hydraulic agitation can only reach 40 to 42 degrees Celsius. Simultaneous heating is needed to make the retting the temperature reach 55 degrees Celsius.

The organic garbage are retted after being crushed can reduce production of sludge; therefore, there is no need to discharge the sludge in a month of operation. When the outputting material has a high content of phosphorus and nitrogen, a certain carbon source can be added to adjust the content of phosphorus and nitrogen.

Embodiment 3 An experiment to test the capability of the sewage gas generating device.

According to the method of the present patent application, the sewage gas generating device includes two tanks connected to each other in series and a centrifugal pump with a flow rate of 4 T/h and a lift of 15 m. The centrifugal pump is used to provide the internal reflow.

The flow rate of the hydrolytic and acidifying liquid retted by the retting process is 2.5 T/h, and the flow rate of the upper clear liquid is 1 T/h, therefore, the combined flow rate is 3.5 T/h. The flow rate of the bottom sludge and the bottom liquid is 0.5 T/h. The bottom sludge and the bottom liquid are conveyed back to the pretreatment tank 2#A by the Nikuni pump as the anaerobic sludge to adjust and improve the separation of the pretreatment. The valve is opened to convey the scum which needs to be re-retted, and the flow rate is 0.5 T/h. The quantities of the inputted material for 10 days and the quantities of the outputted material after 10 hours of each inputting time are tested to obtain the sewage gas treatment and producing capacities of the sewage gas generating device. The tested data are shown in the following table 10.

TABLE 10

| Number of days | COD of the input liquid | COD of the output liquid | Removal rate of COD | SS of the input liquid | SS of the output liquid | Removal rate of SS | pH of the output liquid | Amount of the sewage gas (m³) | temperature |
|---|---|---|---|---|---|---|---|---|---|
| 1 | 1059 | 296 | 72% | 1480 | 365 | 75% | 7.5 | 31 | 35 |
| 2 | 1061 | 201 | 81% | 1195 | 206 | 83% | 7.9 | 35 | 35 |
| 3 | 1059 | 233 | 78% | 1555 | 222 | 86% | 7.8 | 34 | 35 |
| 4 | 1059 | 95 | 91% | 1290 | 411 | 68% | 7.3 | 40 | 35 |
| 5 | 1589 | 96 | 94% | 998 | 180 | 82% | 7.4 | 60 | 35 |
| 6 | 2118 | 21 | 99% | 1685 | 330 | 80% | 6.5 | 87 | 35 |
| 7 | 2118 | 127 | 94% | 1100 | 311 | 71% | 6.8 | 82 | 35 |
| 8 | 2859 | 143 | 95% | 1160 | 310 | 73% | 6.7 | 102 | 35 |
| 9 | 3177 | 127 | 96% | 1810 | 290 | 84% | 6.8 | 125 | 35 |
| 10 | 3707 | 112 | 97% | 1780 | 290 | 83% | 6.6 | 148 | 35 |
| Average | 1769 | 145 | 91% | 1403 | 292 | 79% | 7.1 | 74 | 35 |

The living things in the sewage gas generating tank are mainly methanogenic bacteria. The sewage gas generating device uses a fixed bed as carrier of living things to prevent loss of thallus. Because the growth speed of the methanogenic bacteria is very slow, the data in table 10 shows that the increased production volume of sewage gas is related to the quantity of the methanogenic bacteria in the sewage gas generating tank.

In this experiment, the samplings of the scum and the bottom sludge are tested. The tested values of the SS in the scum and the bottom sludge are over 4000 mg/L, showing that the methanogenic bacteria has no effect on the degradation of the SS and the removal of the SS in the sewage gas generating tank mainly depends on the re-retted scum and the returned sludge. The SS are removed in the retting tank by the circulation.

The sewage gas generating tank can not reduce the quantities of nitrogen and phosphorus, the T/N and T/P values of the input liquid are almost the same as that of the output liquid. The only difference between the input liquid and the output liquid is that the value of the ammonia nitrogen of the output liquid is higher than that of the input liquid.

The sewage gas generating tank has very good thermal insulation; therefore, when the temperature reaches 35 degrees Celsius, the heating device can be removed.

The relationship of the production of the sewage gas and the COD in the sewage gas generating tank is shown in the following formula:

The amount of input liquid $V=3.5$ T/h×24=84 T

The amount of removed COD $M=84\times(1769-145)=$ 136 KG

The amount of produced sewage gas $G=136/74=1.84$ Kg·COD/M³

Embodiment 4 An experiment to test the capability of the biological denitrification and dephosphorization device.

According to the method of the present patent application, the biological denitrification and dephosphorization device includes two tanks (tank A and tank B) connected to each other in series, a pump returning the water with a flow rate of 15 T/h, and a pump returning the sludge from tank A to tank B with a flow rate of 0.5 T/h. The detailed flowchart is shown in FIG. 17.

The flow rate of the input liquid is 10.5 T/h, and the daily production of the biological denitrification and dephosphorization device is 250 T/d. The COD, T/N, T/P, SS values of the input liquid and the output liquid are tested every 8 hours, and the producing equivalents N of the two tanks are calculated according to the tested values. The phosphorus sludge is mainly in the bottom sludge of the tank B, and the phosphorus removal mainly depends on discharging the bottom sludge. The amount of phosphorus in the bottom sludge is $P_1$ (in units of mg/L), the removal equivalent of phosphorus of the biological denitrification and dephosphorization process is $P_2$ (in units of Kg/d), the daily amount of discharged sludge $V=P_2/P_1\times 10^3$. In this embodiment, $P_1$ is 1000 mg/L, $P_2$ is 11.77 Kg/d, and V is 1.18 m³/d, therefore, the valve can be opened about 3 minutes to discharge the sludge, and the amount of discharged sludge can reach 1 m³.

TABLE 11

| Test data | | | | |
|---|---|---|---|---|
| Times of testing the upper clear liquid | COD | T/N | T/P | SS |
| 1 | 208 | 17 | 12.2 | 156 |
| 2 | 214 | 23 | 14.1 | 203 |
| 3 | 200 | 19 | 11.5 | 180 |
| 4 | 260 | 21 | 13.8 | 166 |
| 5 | 272 | 32 | 14.5 | 240 |
| 6 | 186 | 16 | 10.8 | 138 |
| 7 | 168 | 18.5 | 12.3 | 120 |
| 8 | 235 | 22.5 | 11.9 | 148 |
| 9 | 204 | 26 | 17.2 | 148 |
| 10 | 238 | 33.5 | 18 | 165 |
| 11 | 188 | 15 | 15.6 | 176 |
| 12 | 204 | 19.5 | 16.4 | 188 |
| Average | 215 | 22 | 14 | 169 |

TABLE 12

| Times of testing the sewage liquid | COD | T/N | T/P | SS |
|---|---|---|---|---|
| 1 | 206 | 299 | 180 | 305 |
| 2 | 266 | 320 | 144 | 460 |
| 3 | 302 | 285 | 156 | 288 |
| 4 | 210 | 199 | 198 | 290 |
| 5 | 460 | 330 | 136 | 312 |
| 6 | 421 | 286 | 167 | 304 |
| 7 | 338 | 198 | 203 | 308 |
| 8 | 211 | 197 | 149 | 411 |
| 9 | 196 | 184 | 210 | 376 |

TABLE 12-continued

| Times of testing the sewage liquid | COD | T/N | T/P | SS |
|---|---|---|---|---|
| 10 | 184 | 212 | 118 | 246 |
| 11 | 234 | 168 | 98 | 258 |
| 12 | 218 | 293 | 140 | 327 |
| Average | 270.5 | 247.5 | 158 | 324 |

TABLE 13

| Times of testing the output liquid | COD | T/N | T/P | SS |
|---|---|---|---|---|
| 1 | 102 | 6.6 | 3.5 | 16 |
| 2 | 112 | 9.8 | 4.1 | 25 |
| 3 | 98 | 6.2 | 4 | 12 |
| 4 | 46 | 4.3 | 3.2 | 12 |
| 5 | 51 | 0 | 1.4 | 14 |
| 6 | 40 | 2 | 1.1 | 12 |
| 7 | 78 | 1 | 0.8 | 7 |
| 8 | 64 | 2 | 0.55 | 7.5 |
| 9 | 43 | 0 | 0.45 | 6.8 |
| 10 | 55 | 0 | 0.42 | 9.2 |
| 11 | 41 | 1.2 | 0.38 | 5.5 |
| 12 | 38 | 0 | 0.4 | 7.4 |
| Average | 64 | 2.8 | 1.7 | 10.6 |

TABLE 14

The amounts of the input liquid and the output liquid per hour are converted to a total value in the unit of kg/d, and the rate of the treatment (%) and the equivalent of the treatment (Kg/d) are shown in the following table.

|  | COD | T/N | T/P | SS |
|---|---|---|---|---|
| Total amount of the upper clear liquid | 41.2 | 4.2 | 2.7 | 32 |
| Total amount of the methane liquid | 16.2 | 14.8 | 9.5 | 19 |
| Total amount of the input liquid | 57.4 | 19 | 12.2 | 51 |
| Total amount of the output liquid | 1.7 | 0.7 | 0.43 | 2.7 |
| Rate of the treatment | 97% | 96.3% | 96.5% | 94.7% |
| Equivalent of the treatment | 55.7 | 18.3 | 11.77 | 48.3 |

The denitrification and dephosphorization device has a good removal rate on COD, T/N, T/P, and SS, and especially on the removal of the nitrogen. The theoretical value of C/N/P=100/5/1 calculated by a conventional method does not apply to the device. The C/N/P=100/33/21 calculated for the present patent application shows the denitrification and dephosphorization device can treat the domestic sewage with high concentration of nitrogen and phosphorus. Because of the fixed bed comprised by the fiber to grow the anoxic living things and the anaerobic living things, and the denitrification and dephosphorization device can adjust the lengths of the reaction times of the anoxic reaction and the anaerobic reaction, which solves the competition over the carbon source in the nitrogen and phosphorus removal processes.

The re-retting process can help reduce the pressure of the treatment of the SS by the denitrification and dephosphorization device. The tested value of the SS in the re-retted sludge is higher than 40000 mg/L, showing that the SS can be removed by the retting device in a re-retted process. And that is also a main factor for effective dephosphorization.

The tested average value of the T/P in the re-retted sludge is higher than 10000 mg/L, to prevent the phosphorus being gathered in the system and reduce the T/P value of the output liquid, the re-retted sludge should be discharged out of the system in time. The tested value shows that if the re-retted sludge is discharged for 3 minutes daily, the total amount of the discharged re-retted sludge can reach 1 m$^3$, and that can make the T/P value of the output liquid reach the discharge standard of 0.5 mg/L. The pump of the secondary deposition tank can return the water and sludge in time to make the secondary deposition tank have a good settlement and separation effect. The average value of SS in the output liquid discharged by the biological denitrification and dephosphorization device is 10, and the SS in the output liquid discharged by the secondary deposition tank is 2 to 6 mg/L.

The above embodiments show that the method for treating domestic sewage and organic garbage of the present patent application is realizable. The retting process and the re-retting process are very important to treat the domestic sewage and organic garbage. The system of the present patent application has a small size and can treat the domestic sewage and organic garbage without leaking and secondary pollution. Furthermore, the amount of the discharged sludge is very little. The amount of the discharged sludge with water is about 1 m$^3$/d, and the amount of the discharged sludge without water is about 20 Kg/d. The discharged sludge can be used as phosphate fertilizer, without secondary pollution. The organic garbage can be treated effectively, and that has economic, environmental and social significance.

The system of the present patent application can use the biological sludge collected from a common domestic sewage treatment plant, because the biological sludge can help treat the domestic sewage and organic garbage after the biological sludge has been cultured and domesticated. Some kinds of bacteria can be added in the biological sludge to help treat some special domestic sewage by the system and method of the present patent application.

Figure 18:
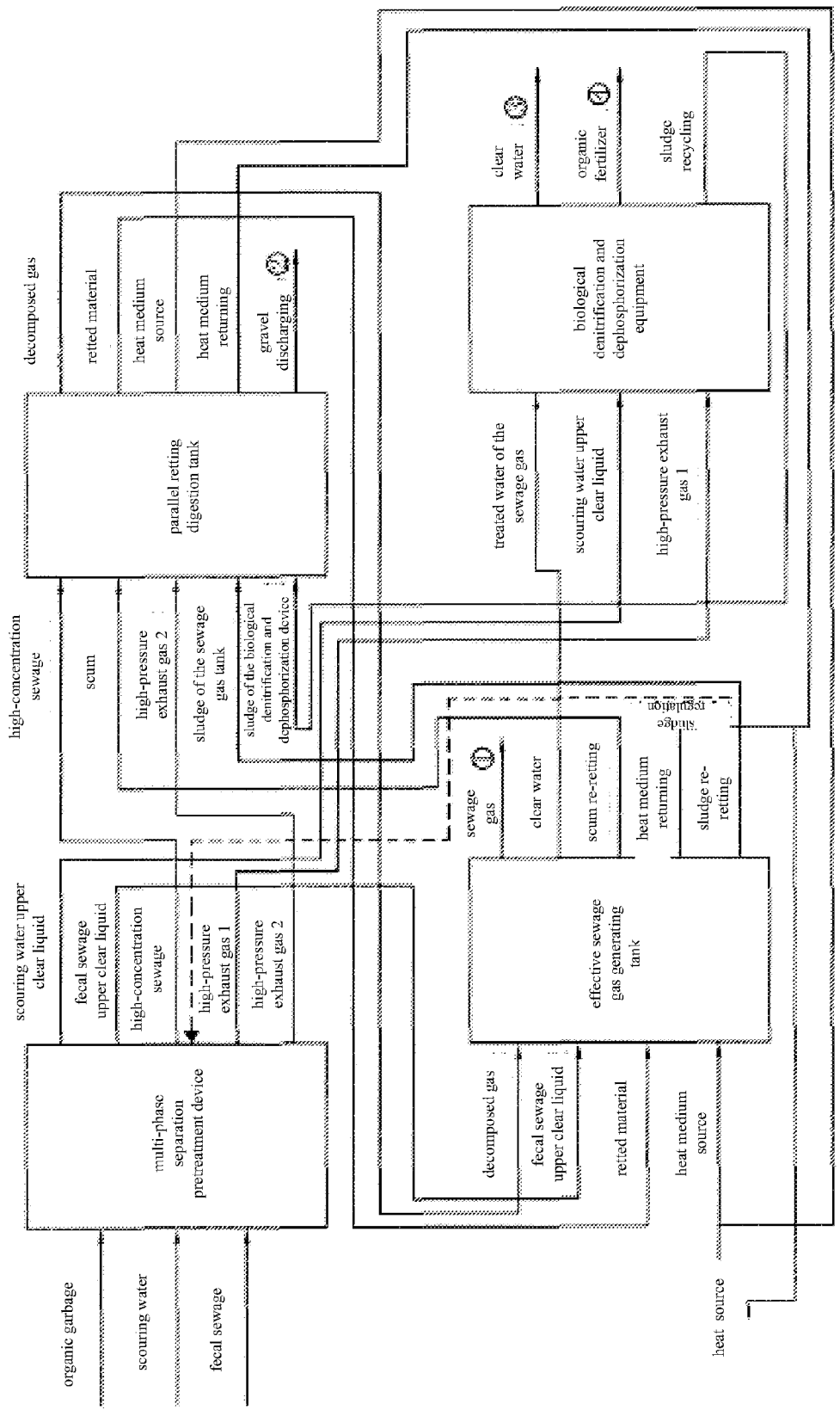
FIG. 18 is a flowchart of the method of FIG. 1 preformed by a system for treating domestic sewage and organic garbage.
Figure 19:
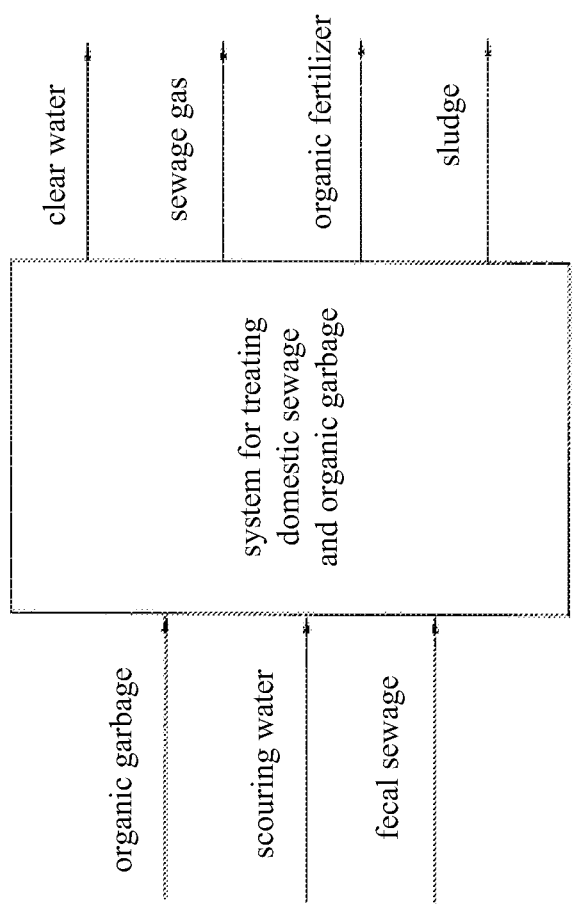
FIG. 19 is a block diagram of the system for treating domestic sewage and organic garbage.

The method for treating domestic sewage and organic garbage of the present patent application uses multi-phase separation, retting, generating sewage gas and biological denitrification and dephosphorization to treat the domestic sewage and organic garbage, as shown in FIG. 18. The organic garbage, the fecal domestic sewage and the scouring water can be converted to clear water, sewage gas, organic manure and sludge by the treatment of the system of the present patent application, as shown in FIG. 19. The method of the present patent application also solves the problem of discharging methane gas from the septic tank, so as to reduce the workload of the environmental protection department. It is also solves the problem of treating the organic garbage and reduces the pressure of the landfilling area. Therefore, the environment protection purpose of comprehensive treatment and minimum pollution emission can be achieved.

The system for treating domestic sewage and organic garbage of the present patent application can be used widely, such as in the applications as follows.

The system can be used in urban residential construction and renovation. Divided by the residential area, the domestic sewage and partial domestic garbage of each community is discharged in situ with minimum pollution due to the use of the technology and equipment of the present patent application. The pollutant discharge fee of the urban residents and the environmental financial expenditure of the government can be reduced due to the small investment of the equipment and long-term benefits.

The system can be used in the processing of domestic sewage and domestic garbage around river basins and lakes surrounding areas. The water treated by the system for treating domestic sewage and organic garbage of the present patent application can be discharged into rivers and lakes directly. It is especially suitable for water system developed regions, which implements the local domestic sewage treatment discharge, so as to avoid the construction investment of the domestic sewage pipe network below the river network and reduce the huge investment of cities and towns faced in the process of the environment transformation.

The system can be used in the pasture of remote areas. It will decompose livestock manure rapidly, so the problem of methane emissions and poor power in these areas are solved. Meanwhile, the treated water can also solve the drinking water for livestock. The use of large amounts of organic fertilizers can restore the natural ecosystem of the grassland.

The system can be used for suburban and rural areas. Precision agriculture can be developed by the use of the rich organic fertilizer, such as organic farming, organic fruits vegetables and etc. The water discharged by the biogas tans can be used as fertilizer directly without the processing of denitrification dephosphorization equipment, when the present patent application is used in these areas. It is a kind of ecological compound fertilizer that the sewage gas water containing ammonia nitrogen and water soluble phosphate ingredients produced under anaerobic condition with 35 degrees Celsius, the trace amounts of organic phosphorus composition of which has a natural insecticidal effect, which can reduce the dependence on chemical fertilizers and pesticides in rural areas. The washing supernatant fluid is used in the irrigation network directly, which can reduce the pressure of rural irrigation water.

The system can be used in the rural and mountainous areas of power shortage. Gasoline/marsh gas dual power can be used in the system for treating domestic sewage and organic garbage of the present patent application. The device starts with petrol power generation, and switch to sewage gas power generation when the generation of the sewage gas, and then the device can run continuously. To a certain extent, it can solve the electricity and fuel problems of these areas.

The system can be used for domestic sewage and waste treatment in slaughterhouse, food engineering and distillery. The system of the present patent application can effectively deal with domestic sewage of high fat, high protein, high starch, high carbohydrate and waste of the same. The treated water is used as flushing water in plant, so as to achieve water recycling.

The system can be used for hospital independent domestic sewage treatment equipment. The system of the present patent application can effectively deal with the hospital discharged domestic sewage with pathogens, bacteria and viruses, which can be directly discharged after sterilization. It is the best way of harmless handling medical waste water that the fully closed processing equipment is used. The equipment can adopt municipal power supply, and the sewage gas produced is used to generate hot water for hospitals by a boiler.

The system can be used for the governance and reform of landfilling areas. The landfilling garbage is excavated to be flushed, and the digestible organic waste is crushed and mixed with the flushed domestic sewage. The clean water produced by the present patent application can be used for recycling the flushing water. The sewage gas produced can be used for drying non-digestible garbage for recycling or retreatment. The discharged reduction grit and biological sludge are dumped in landfills or incinerated.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for treating domestic sewage and organic garbage, the method comprising:
    (a) multi-phase separation: separating the domestic sewage into upper clear liquid, upper floating liquid, sediment liquid, grating separated substances, and exhaust gas through a multi-phase separation process, mixing and crushing the upper floating liquid, the grating separated substances and the organic garbage to form a mixture, and mixing the sediment liquid with the mixture to form high-concentration sewage;
    (b) retting: retting the multi-phase separated high-concentration sewage to form retted material;
    (c) generating sewage gas: using the upper floating liquid of the domestic sewage and the retted material to generate sewage gas and then discharging the sewage gas; and
    (d) optional biological denitrification and dephosphorization: treating at least one of the water generated in step (c) and the upper clear liquid obtained in step (a) with a biological denitrification and dephosphorization process, and discharging clean water and organic fertilizer.

2. The method of claim 1, wherein the domestic sewage comprises at least one of fecal sewage and scouring water.

3. The method of claim 1, wherein the step (c) comprises at least three retting digestion units connected in parallel with each other.

4. The method of claims 1 further comprising:
    (e) re-retting: returning scum that is difficult to be digested in steps (c) and (d) to the step (b) and retting the scum again.

5. The method of claim 1 further comprising:
    (f) bottom sediment and bottom liquid returning: returning the bottom sediment and the bottom liquid produced in step (c) to the step (a) to perform an anaerobic sludge regulation.

6. The method of claim 1, wherein the ratio between the amount of the mixture of the upper floating liquid and the sediment liquid and the total amount of water in step (a) is not more than 5%.

7. The method of claim 1, wherein the exhaust gas produced in step (a) is used in aeration agitation during an initial stage of the step (b).

8. The method of claim 1, wherein heat generated in steps (b) and (c) is used in the thermal cycling of the system.

9. The method of claim 1, wherein the step (b) comprises: inputting materials, retting reaction, and outputting materials, state of each retting device will not be affected by the other retting devices.

10. The method of claim 9, wherein the retting reaction is performed under agitation.

11. The method of claim 9, wherein at an initial stage of the retting reaction an external heat source is used to heat, then the heating is stopped, and the reaction temperature continues to rise utilizing the heat spontaneously generated by the retting reaction.

12. The method of claim 11, wherein the external heat source stops heating when the temperature reaches 55 degrees Celsius.

13. The method of claim 9, wherein the reaction time of the retting reaction is 2 to 3 days.

14. The method of claim 1, wherein the reaction temperature of the step (c) is 35 degrees Celsius with a precision of ±1 degree Celsius.

15. The method of claim 1, wherein in the step (c), methane bacteria are mainly used.

16. A system for treating domestic sewage and organic garbage, the system comprising:
- a multi-phase separation device;
- a retting device;
- a sewage gas generating device; and
- an optional biological denitrification and dephosphorization device, the multi-phase separation device, the retting device, the sewage gas generating device and the optional biological denitrification and dephosphorization device being connected to one another in series, wherein the sewage gas generating device defines a scum re-retting exit communicated with the retting device and a sludge regulation exit communicated with the multi-phase separation device, the scum re-retting exit and the sludge regulation exit being configured for scum re-retting and sludge regulation respectively; wherein the multi-phase separation device further defines an exhaust gas exit communicated with an inner cavity of a mixture crusher via a grating separation channel, so that a feeding port of the mixture crusher is in a negative pressure state.

17. The system of claim 16, wherein the multi-phase separation device defines an exhaust gas exit communicated with the biological denitrification and dephosphorization device.

18. The system of claim 16, wherein each retting digestion tank comprises a powerful gas agitator.

19. The system of claim 16, wherein the multi-phase separation device further comprises a blower to convey exhaust gas.

20. A multi-phase separation device for separating domestic sewage, the multi-phase separation device comprising: a domestic sewage entrance, a gravel separation chamber, a gravel exit, an auto-separating grating machine made of an irregular-shaped grating and a separation rake, a grating separated substance exit, an upper floating chamber, an upper clear liquid chamber, and an optional upper clear liquid regulation tank connected to the upper clear liquid chamber, wherein the upper floating chamber comprises at least one of a micro-bubble producer and a sludge regulation releaser at a middle portion of the upper floating chamber.

21. The device of claim 20 further comprising a clapboard located between the upper floating chamber and the upper clear liquid chamber, the bottoms of the upper floating chamber and the upper clear liquid chamber being communicating with each other.

22. The device of claim 21, wherein the volume of the upper clear liquid chamber is not less than that of the upper floating chamber.

23. The device of claim 22, wherein a ratio of the volume of the upper clear liquid chamber to the volume of the upper floating chamber is 3.

24. The device of claim 20, wherein the irregular-shaped grating comprises a vertical section, an arc section and a slant section.

25. The device of claim 20, wherein the pitch of the grating is less than 4 millimeters.

26. A multi-phase separation method for separating domestic sewage, the method comprising:
- (a) separating gravel from the domestic sewage by a sloping method;
- (b) obtaining grating separated substances by separating with an irregular-shaped grating;
- (c) adsorbing floating substances in the vertical down-flowing sewage by micro-bubbles produced by a micro-bubble producer to form upper floating liquid, and then draining off the upper floating liquid; and/or using the sludge to regulate and absorb the organic pollutants to form upper floating liquid with a lighter specific gravity, and then draining off the upper floating liquid;
- (d) changing orientation of the down-flowing sewage at the bottom of a clapboard located between an upper floating chamber and an upper clear liquid chamber, so that the sewage flows into the upper clear liquid chamber while the sediment stays at a bottom, and then draining off the sediment liquid; and
- (e) draining off the upper clear liquid formed by the up-flowing sewage.

27. The method of claim 26, wherein the up-flowing distance or the down-flowing distance of the sewage is more than 5 meters.

* * * * *